(12) United States Patent
Boehm, Jr.

(10) Patent No.: US 10,687,866 B2
(45) Date of Patent: Jun. 23, 2020

(54) SPINAL STABILIZATION WITHOUT IMPLANTATION OF HARDWARE INTO THE VERTEBRAE PROPER OR VIOLATION OF CORTICAL BONE

(71) Applicant: Frank H. Boehm, Jr., New Hartford, NY (US)

(72) Inventor: Frank H. Boehm, Jr., New Hartford, NY (US)

( * ) Notice: Subject to any disclaimer, the term of this patent is extended or adjusted under 35 U.S.C. 154(b) by 0 days.

(21) Appl. No.: 15/646,615

(22) Filed: Jul. 11, 2017

(65) Prior Publication Data

US 2017/0319238 A1 Nov. 9, 2017

Related U.S. Application Data

(63) Continuation of application No. PCT/US2016/013030, filed on Jan. 12, 2016.

(60) Provisional application No. 62/102,581, filed on Jan. 12, 2015.

(51) Int. Cl.
*A61B 17/70* (2006.01)

(52) U.S. Cl.
CPC ........ *A61B 17/707* (2013.01); *A61B 17/7047* (2013.01); *A61B 17/7067* (2013.01)

(58) Field of Classification Search
CPC ............ A61B 17/7062; A61B 17/7064; A61B 17/7067
USPC .................................................. 606/246–249
See application file for complete search history.

(56) References Cited

U.S. PATENT DOCUMENTS

| 4,570,618 A | 2/1986 | Wu |
| 5,374,267 A * | 12/1994 | Siegal ................ A61B 17/7049 606/250 |
| 6,132,464 A | 10/2000 | Martin |
| 6,589,243 B1 | 7/2003 | Viart et al. |
| 2002/0151895 A1 * | 10/2002 | Soboleski .......... A61B 17/7064 606/247 |
| 2006/0241614 A1 | 10/2006 | Bruneau et al. |

OTHER PUBLICATIONS

ISA/US; International Search Report/Written Opinion dated Mar. 17, 2016 in International Application PCT/US16/13030.

* cited by examiner

*Primary Examiner* — Julianna N Harvey
*Assistant Examiner* — Christina Negrellirodriguez
(74) *Attorney, Agent, or Firm* — Christopher E. Blank; Schmeiser, Olsen & Watts, LLP

(57) ABSTRACT

A device and method for use which stabilizes a target motion segment of the spine without the use of screws or any form of hardware implanted into the vertebrae. By being comprised of modular segments and assembled onto the target motion segment at the time of implantation, it can be provided in kit form designed for each patient. The stabilization apparatus general comprises elements; one is adjustably secured to the posterolateral aspect of the caudal vertebra of the target motion segment, with another element being secured to the base of the spinous process of the cranial vertebra of the target motion segment. These two elements are then coupled to each other by either an elongated rod-like connecting element, or extensions from the two anchoring elements which then couple.

5 Claims, 18 Drawing Sheets

SPINAL STABILIZATION WITHOUT IMPLANTATION OF HARDWARE INTO THE VERTEBRAE PROPER OR VIOLATION OF CORTICAL BONE

CROSS-REFERENCE TO RELATED APPLICATIONS

This application claims priority to and is a continuation of international patent application PCT/US16/13030 (filed Jan. 12, 2016) which claims priority to non-provisional of U.S. Patent Application Ser. No. 62/102,581 (filed Jan. 12, 2015), the entirety of which is incorporated herein by reference.

BACKGROUND OF THE INVENTION

There are many causes for back pain, including systemic disorders, tumors, and infections, but by far the most common cause is degenerative disease. This disease process is especially prominent in the lower lumbar spine, most commonly affecting the L4-L5 and L5-S1 levels.

A recent study from the American Chiropractic Society demonstrates that on average, 31 million Americans seek help for back pain annually. This number is growing for a number of reasons including, tobacco use, the increasing participation of Americans in contact sports and physical activity as well as the advancing age of American society. The vast majority of these patients are easily treated with conservative management such as Chiropractic adjustment, physical therapy, Massage therapy, and other techniques. However, a subset of patients with back pain will not respond to this type of treatment and are referred for surgical evaluation.

Much is yet to be learned in terms of the physiology and pathophysiology of the spine, and at present, a well-accepted paradigm is the so-called spinal motion segment. This refers to any particular pair of adjacent vertebrae along with the intervening disc and associated muscles, tendons, ligaments, and neurovascular structures. By evaluating any particular motion segment, thus better understanding the normal and abnormal movements at one level, one can better understood the spine as a whole, particularly when viewed as a series of adjacent motion segments rather than merely a vertically stacked series of vertebrae.

It is felt that one problem in degenerative disease is that there is excessive or abnormal movement between the vertebrae of one or more spinal motion segments. This is the basis for proposing surgical fusion, used for over 100 years now, which is a procedure in which the surgeon creates a milieu which encourages the development of a bony bridge between the vertebrae of a target motion segment, thus uniting these vertebrae into one large vertebra. Such a union would obliterate all movement at the target motion segment. Ultimately, approximately 400,000 patients annually undergo surgical fusion of the spine in the United States alone, with more than a million performed globally. These numbers have been fairly stable over the past decade.

Unfortunately, between 15 and 30% of such surgeries do not result in an outcome that the patient is satisfied with, and in fact a significant number of these patients report significant worsening of their symptoms. This syndrome, known as the so-called "failed back surgery syndrome," or "post laminectomy syndrome," is characterized by severe, chronic unrelenting pain which is poorly responsive to almost any intervention, as well as rather significant disability, and almost always associated with progressive severe depression and poor socialization. There are many thousands of such patients currently here in America, and this patient population creates an enormous drain on the health care delivery system. A system or device that would reduce this patient population would be of enormous value to the system.

Current technologies for establishing diagnoses all have shortcomings. Theoretically, the ideal patient who would optimally benefit from surgical fusion would be a patient who has a degenerative disease affecting a particular spinal motion segment in which it can be clearly shown that this spinal motion segment demonstrates an excessive I pathologic amount of movement, and that this movement is the genesis of the patient's pain—the so-called "pain generator."

Despite the superb imaging and diagnostic tools which are now available to physicians and surgeons, demonstrating that this abnormal movement is unambiguously present, proving that this movement is responsible for at least the majority of the patient's symptoms remains remarkably challenging.

In addition to X-Rays and CAT scanning techniques, MRI scans have become the platinum standard for establishing diagnoses for the spine. But this has also been shown to have its shortcomings, principally in the fact that MRI studies demonstrate at times significant degenerative changes in patients that are asymptomatic. Therefore, identifying such changes in a patient who is symptomatic does not absolutely establish a causal relationship between the MRI findings and the patient's symptoms. This can sometimes lead to conclusions by both patients and surgeons, and sometimes results in such patients undergoing fusion surgery which does not relieve the patient's symptoms, and sometimes results in worsening of these symptoms.

This is because in additional to mechanical causes or pain—mechanical pain generators—there are other causes of back pain. It is well-known that there can be chemicals which are released locally which can lead to so-called "chemical pain generators. These may or may not be related to abnormal movements, so that stabilizing the spine with a fusion might, but is not guaranteed, to improve the pain.

Other issues that make back pain even more difficult to diagnose and treat include the fact that in many technologically-advanced countries, in particular the United States, back pain is frequently associated with injuries sustained in motor vehicle accidents, other injuries in which third parties are actionably responsible, or as the result of work related injuries. Such scenarios frequently result in litigation, resulting in the well-known phenomenon known as "secondary gain" causes of back pain. It is well documented that in many of these patients, only the favorable resolution of the associated litigation will result in a favorable resolution of the back pain.

A number of other pain generators have been identified or are alluded to, and added to that, it is well-known that back pain is a common complaint in patients who suffer from a phenomenon known as somatization disorder. This is a clinical situation in which a patient experiences and complains of back pain, and sincerely believes they are suffering from back pain, but ultimately the pain is not found to be related to any identifiable pathoanatomic or pathophysiologic derangement. It is important to recognize that this disorder is different and distinct from the "secondary gain" phenomena discussed above, nor it is related to malingering disorders or other issues in which the patient is cognizant that he or she is amplifying the symptoms; in somatoform disorder, the patient sincerely believes, in his or her soul, that he or she is suffering from some untreatable or rare disorder. Fusing such an individual will, without exception, result in disaster.

Therefore, sorting these issues out and determining who would be best served by a surgical fusion is ultimately more challenging than it may initially appear. The concept of "functional" MRI studies, which would demonstrate whether pain signatures are present on these specially-programmed MRI studies, has been proposed for some time now, and may help resolve some of these issues. While this may have significant value in years ahead, it is likely that this technology will have to undergo multiple scientific and legal challenges before it is fully accepted.

Another method which has been utilized, in one form or another, for many years in determining candidates for fusion surgery is discography. First introduced in 1948, this technique involves passing a needle into a target disc space and introducing X-Ray contrast into the disc space. The criteria by which the test is judged include the pressure required to inject the disc space, the radiologic appearance of the contrast as it flows into the disc space, and the symptoms reported by the patient at the time of the injection.

The value of discography has been a source of controversy for many years, and recently, has been under attack. Several studies have recently shown that injection of "normal" disc space can accelerate disc degeneration, and in fact, it is thought that this technique may precipitate degeneration in discs which may not have otherwise developed pathology.

Several basic science studies have suggested that passing a needle through the annulus fibrosus (the cartilaginous ring surrounding the outside of the disc) can—in and of itself—lead to disc degeneration; this is thought to be true even if nothing is actually injected into the disc space. This may be related to a humoral response to the insertion of the needle, with this humoral response triggering the degenerative process. If this can be shown to be unambiguously true, then this technique will likely be abandoned.

At one point, it was suggested that patients who might be candidates for fusion be placed in a back brace or possibly even a body cast to determine their response to stabilization. There are several problems with this approach. Firstly, there is good evidence that even a very secure body cast allows a significant amount of subtle movement between vertebrae, and does nothing to prevent microinstability from occurring. Secondly, it can be argued that prolonged periods (weeks to months) in a brace, and especially in a body cast (which cannot be removed by the patient) can have deleterious effects including a reduction of muscle tone (which itself can lead to back pain) as well as skin irritation such as blistering and contact dermatitis, generalized deconditioning of the soft tissues of the spine, and other problems. This host of issues often occurs, and added to that is the fact that such a device may not answer the critical questions: Is the patient's spine unstable? Is this instability the main cause of the patient's symptoms? And [ultimately] is fusion indicated?

Therefore, it remains necessary to develop a device and method which would allow a surgeon to transiently (over a period of a few weeks to several months) stabilize the spine in a manner that imitates the effects of a fusion. Such a device would, of necessity, have to provide immediate and secure stabilization Such a device would stabilize a target motion segment in a fashion that would emulate a fusion, allowing the physicians attending to the patient to evaluate the patient's response to this type of stabilization over a period of time (weeks to months). In such a trial, if relief is reported, then the patient could be offered fusion. If the patient reported no improvement, or—of even greater importance—worsening of the symptoms, then the device could be removed and the patient would be informed that fusion should not be considered. Such a device would be unique, useful, novel and nonobvious.

BRIEF DESCRIPTION OF THE INVENTION

The invention relates to the general field of spinal surgery and specifically to a device which is implanted onto a target motion segment in such a way so as to stabilize said target motion segment without requiring hardware, such as screws, to be implanted into the component vertebrae.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

SUMMARY OF THE INVENTION

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The principal object of the invention is to provide a unique, useful, novel and nonobvious device and method for use which is secured against the bony surfaces of a target motion segment of the spine, thus stabilizing said target motion segment. The invention achieves stabilization of a segment of the spine b without the use of pedicle screws, facet screws, spinous process plates or screws, staples, or any form of hardware secured into any aspect of the target vertebrae resulting in violation of the cortical bone of the vertebrae comprising the target motion segment. It is yet a further object of the invention is to disclose the design of the preferred and alternative embodiments of such a device In the preferred embodiment, the Spinofacet Stabilizer shall be fabricated from surgical grade titanium. However, alternatively, this Stabilizer can be fabricated from surgical grade stainless steel, or of alloys of any metal such as molybdenum, chromium, nickel, as well as cobalt, carbon fiber, polyester, ceramic, PEEK, organic materials such as bone, or any other material currently known or proven to be acceptable to the art.

The invention will be best understood by providing the reader with at least a rudimentary review of the pertinent anatomy. This can be appreciated by referring to FIGS. 21-26. These figures demonstrate a typical lumbar vertebral motion segment—in the example used it is the L4-L5 motion segment. The L4 and L5 vertebrae can be seen in various projections, along with the associated intervertebral disc. Nerves, muscles, tendons and ligaments are also components of the motion segment, but are not illustrated for the purposes of simplicity. The articulation of any two vertebrae is accomplished anteriorly by the intervertebral disc (not well seen in the posterior view and best seen in Background FIG. 22) which is a specialized joint—defined by the fact that the disc serves as the junction between two bones (the vertebral bodies) and provides at least an element of movement between the two bones. Posteriorly, the articulation of the two vertebrae is accomplished by the paired facet joints which are located bilaterally as seen in the posterior view in FIG. 22

Figure 25:
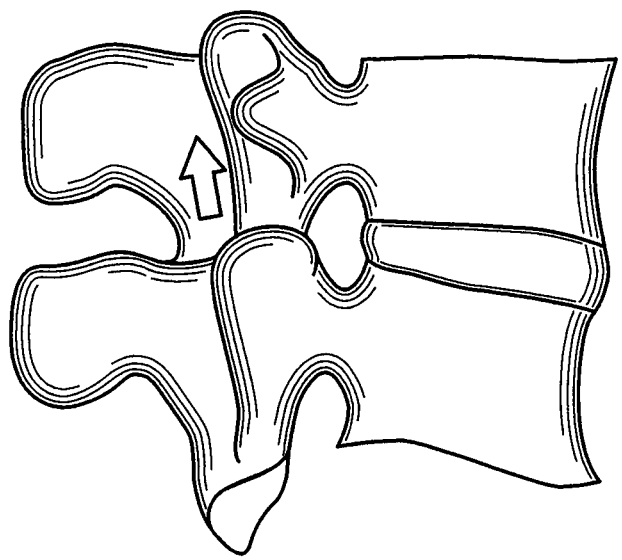
FIG. 25 & FIG. 26 are lateral views demonstrating the reciprocal relationship of the facet joints and disc during (A) Flexion (B) Extension.
Figure 26:
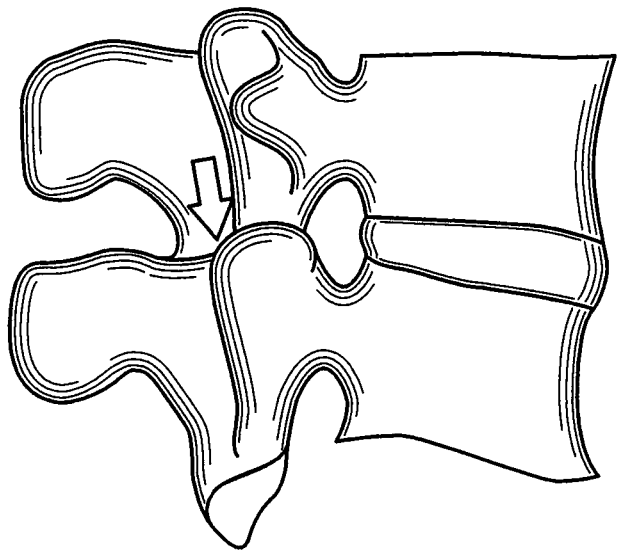

As seen in FIG. 25, these joints are comprised of the lateral-most aspects of the laminae of the superior vertebra of the motion segment, which forms a somewhat rounded almost hemispheric structure known as the inferior articular process; this, then, articulates with the cup-like superior articular process which is formed on the sides bilaterally by the junction of the dorsalmost or most posterior aspect of the pedicle and the transverse process of the inferior vertebra of the motion segment. One notes that the nomenclature may appear somewhat confusing. For example, although the "inferior articular process" is actually part of the superior vertebra, and is on the "superior" aspect of the facet joint proper, this structure is nevertheless found at the inferior aspect of this vertebra, and because of this interpretation (naming this component in terms of its position on the vertebra rather than its contribution to the facet joint itself) this component of the facet joint is referred to as the "inferior articular process."

In an analogous fashion, the contribution from the inferior vertebra of the motion segment is referred to as the "superior articular process," despite the fact that it is actually somewhat more caudal in terms of its relationship to the joint space proper. Again, this component is named in terms of its position on the vertebra.

These processes are also referred to as the inferior and superior zygoapophyseal processes. For ease of interpretation, the term "articular processes" shall be utilized in this disclosure.

The broad dorsal aspect of the inferior articular process does not participate m the actual articulation. It is the lateralmost and ventral aspects of the lamina of the upper vertebra which actually interface with the superior articular process of the lower vertebra that creates the joint space proper. As previously mentioned, the lateralmost and ventral aspects of the inferior articular process create a hemispheric profile as seen in the transaxial perspective. This then is accommodated within the superior articular process, which is, in essence, a cup-like structure, specifically designed to accommodate the inferior articular [cup-like] process. The lateral aspect of the superior articular process, then flows into the junction of the transverse process and the dorsal most aspect of the pedicle, creating the "FPT" complex. This is the critical anatomic landmark for implantation of the Facet Anchoring Element. Extending medially from the medial aspect of this cup is a lip that apposes the ventral aspect of the inferior articular process, thus preventing this structure from becoming dislodged and shift anteriorly into the spinal canal. More dorsally, extending superiorly from the lateralmost aspect of this cup is another lip which prevents the inferior articular process from shifting laterally and dislocating laterally from the cup.

Although the facet joints participate in governing a range of different movements, their most important function is to limit extension of the motion segment. The joints also contribute to governing lateral rotation and lateral bending of the spine, and probably work in conjunction with the disc joints in terms of the general governance of all the movements of the spine.

The facet joints contribute to back pain directly because these joints are richly innervated, and hence can be quite painful when injured. There is now considerable evidence that these joints can be relatively easily injured by hyperextension (particularly in the cervical spine), direct [blunt] trauma, and other mechanisms. In addition, these joints are amongst the more common to be subjected to arthritic changes. When such changes occur, the lips disclosed above can become hypertrophied, leading to enlargement of the joints with intrusion into the spinal canal, resulting in consequent spinal stenosis. Such arthropathy is also attended by instability, and other issues.

This review isn't merely an academic exercise. Rather, this permits one to recognize that the junction of the dorsalmost pedicle and the base of the transverse process with the lateral aspect of the superior articular process would be accessible to placement of one component of the device being disclosed herein. Furthermore, this review allows one to appreciate the relationship of the transverse process to the joint, thus rendering this process a site for anchoring the device ventrally. It also becomes apparent that the spinous process of the more superior vertebra of the target motion segment is yet another excellent anchoring locus, hence supporting the logic of the invention.

The invention disclosed shall be known hereinafter as the Spinofacet Stabilizer, and in the preferred embodiment, shall be comprised of an anchoring element which is secured to the spinous process of one of the vertebrae comprising the target motion segment; it is anticipated that in the preferred embodiment, this anchoring element will be secured against the spinous process of the superior or cranial vertebra of the target motion segment. This anchoring element is then coupled with at least one anchoring element which is secured to the FPT complex on at least one side of the second vertebra of the target motion segment; again, it is anticipate that in the preferred embodiment, this will be the inferior vertebra of the target motion segment. Although it is theoretically possible to achieve stabilization by securing a single anchoring element to the second [inferior or caudal] vertebra of the target motion segment, it is anticipated that in the preferred embodiment, and in the vast majority of clinical cases, two anchoring elements will be bilaterally secured to the inferior vertebra. These anchoring elements are coupled to each other by an elongated rod-like connecting feature, which may in fact, represent the connection of elongated features which are provided to one or both of the anchoring elements, or may be a separate element.

In all preferred and alternative embodiments, that anchoring element which is secured to the FPT complex shall be known henceforth as the Facet Anchoring Element, and is designed to be brought into locked, immovable apposition against the bony surface of the posterolateral aspect of the target vertebra; again it is anticipated that this will likely be the lower I caudal vertebra of the target motion segment. A single Facet Anchor can be applied and may result in stabilization, but biomechanical logic favors bilateral application. It is anticipated that bilateral application creates the most secure grasp of the lower vertebra of the target motion segment.

The Facet Anchoring element is itself comprised of two constituent components. The first of these components shall be known as the Facet Base, which is secured against the posterolateral aspect of the caudal vertebra of the target motion segment. Specifically, this component is applied against the confluence of the lateral aspect of the superior facet process as this joins with the dorsalmost aspect of the pedicle, this confluence then joining with the posterior and medial aspect of the base of the transverse process. For the purposes of this document, this target bony confluence shall be referred to as the FPT (facet I pedicle I transverse process) complex.

This Facet Base is provided with a leading end (which is brought into apposition with the FPT complex) a body, and a trailing end (which passes over the posterior aspect of the facet joint proper). As viewed from the lateral perspective, there is a general rhomboid configuration with a slant in the leading end as dictated by the anatomy of the confluence of the transverse process with the posteriormost pedicle. In the preferred embodiment, the trailing end curves over the facet joint, and gives rise to the extension by which the Facet Anchor couples with the Spinous Anchor. This extension shall be known hereinafter as the coupling extension.

As viewed from the frontal (anatomically axial) perspective, in the preferred embodiment, the body of the Facet Base is substantially triangular in configuration, with an expanded and somewhat curvilinear medial aspect of the leading end, which is configured to achieve maximum apposition I interface with the target bony surfaces. It is also appreciated in this frontal I axial view that ideally, the leading end of the Facet Anchor is contoured to recapitulate the contour of the target bony anatomy, and in that way create the greatest interface with the target bony surfaces.

The lateral aspect of the expanded leading end extends onto the proximal aspect of the transverse process. The lateral aspect of the body houses the coupling mechanism of the Facet Base with the other component of the Facet Anchor, which is the Transverse Process Claw. A configuration in which the Transverse Process Claw is disposed from a more lateral aspect towards the medial pedicle is the most biomechanically stable in terms achieving secure apposition of the Facet Anchoring Element.

When viewed from the anatomic posterior view, it is mostly the trailing end of the facet base which is seen; this appears to have a nearly triangular configuration, with the lateral aspect of the base being flattened, and the two sides approaching each other ultimately joining with the coupling extension. It is to be recalled that when viewing the preferred embodiment of the invention from the anatomically posterior perspective, Facet Anchoring elements would ideally be applied bilaterally to the left and right FPT complexes.

As disclosed above, the second component of the Facet Anchoring element is one or more Transverse Process Claws. In the preferred embodiment, this is a monolithic element which is provided with a leading end, a shaft, and a trailing end. The leading end is curvilinear in the preferred embodiment, favorably designed to pass through soft tissues during its placement into its final desired position. Ultimately, it is secured against the surface of the junction of the anterior surface of the transverse process with the lateral aspect of the pedicle (referred to for the purposes of this document as the TPIP junction). In order to provide a greater area of contact, the leading end has a broadened, slightly concave area which is configured to maximally appose the target bony surface area. Maximal apposition may be further achieved by providing the leading end of the Claw with a bias, to further accommodate the slant of the bone as the pedicle conjoins with the transverse process.

The shaft connects the leading end of the Claw to the trailing end; the trailing end is coupled to the Facet Base in such a fashion that the Transverse Process Claw can be brought against the target bony surfaces with maximum security. It is anticipated that this action will also compel the facet base to be brought securely against the FPT complex, the ultimate result causing the two constituent components of the Facet Anchoring Element to become securely locked against their target bony surfaces thus locking the Facet Anchoring Element securely to the posterolateral aspect of the target vertebra in a unique, useful, novel and nonobvious fashion.

Multiple preferred and alternative embodiments of the components of the Facet Anchoring Element and the coupling of these components can be envisioned. In fact, it can be recognized that the Facet Anchoring element has the potential for the greatest number of variations of any of the elements which comprise the Spinofacet Stabilizer. This is because of the potential variations in the Transverse Process Claw, implantation thereof, as well as the manner in which this Claw is coupled with the Facet Base. However, it is understood that those well versed and skilled in the art may envision and conceive of yet other configurations which would achieve such an endpoint. All such embodiments are contained within the spirit and scope of this application for this invention.

In the preferred embodiment of the Facet Anchoring Element, the Facet Base would be substantially configured as described above. A single Transverse Process Claw is irreversibly coupled to the superior I cranial aspect of the Facet Base. An advantage to utilizing a single cranial Transverse Process Claw which is implanted from a superior or cranial approach is that this would virtually eliminate the possibility of injuring the nerve root, which classically escapes from the spinal canal along the caudal aspect of the associated pedicle.

The Transverse Process Claw is coupled to the Facet Base by providing an aperture to the cranial side of the body of the Facet Base, said aperture then being continuous with a chamber within the body. In a corresponding fashion, the trailing end of the Claw is provided with a coupling peg which arises in an orthogonal fashion to the long axis of the trailing end of the shaft of the Claw. The outer diameter of the coupling peg is slightly larger than the inner diameter of the aperture, creating a snug, "pressure-fit" when the peg is inserted through said aperture and into the chamber. This arrangement will establish the coupling peg as the axis of rotation around which the Transverse Process Claw can rotate into the desired position. Moreover, this junction becomes a fulcrum with the two elements of the Facet Anchor acting as lever arms as they are brought against the target bony surfaces. Hence, the coupling of the transverse process claw with the facet base serves as an actuator which, in effect, clamps the Facet Anchoring Element against the posterolateral aspect of the target vertebra. This is more biomechanically stable arrangement in a dynamic biomechanical site such as the spine.

In the preferred embodiment, the leading end of this coupling peg is provided with a series of regularly-spaced corrugations. These corrugations arise generally orthogonal to the long axis of the coupling peg, and are designed to interface with a complimentary series of corrugations which have been provided to the surface of the chamber, which creates a ratcheting mechanism between the peg and the chamber. In the process of implanting the Facet Anchor, the Transverse Process Claw is rotated towards the target bony surface, and said ratcheting mechanism will compel the Transverse Process Claw, and in turn cause the Facet base to be drawn anteriorly and cinched against the FPT complex. Again, this rotation will, in the most ideal of circumstances, also provide secure fixation of the Facet Anchoring element to the posterolateral aspect of the target vertebra.

Of course, the types of the adjustable coupling of the Facet Base with the shaft of the transverse process may include a ratcheting mechanism, a "cold weld" process, or any other process which would result in an adjustable coupling between two components. All such mechanisms would be included within the spirit and scope of the invention.

The second element of the Spinofacet Stabilizer shall be known as the Spinous Anchor, which is a modular element and shall be comprised of at least two or more components which, when adjustably coupled together, create a substantially oval ring which is secured around the base of the spinous process of a target vertebra. In an embodiment utilizing two components, each of these components consists of a hemi-ellipse which are configured such that when coupled together they form an ellipse which can be secured to the base of the target spinous process. In the preferred embodiment, the hemi-ellipses are adjustably coupled, with a ratcheting mechanism or some other adjustable coupling mechanism provided to the hemi-ellipses. It is considered rather important that the components of the Spinous Anchor are adjustably coupled together so that the Anchor can be securely fitted around the spinous process. Therefore, in the preferred embodiment, each of the hemi-ellipses are in turn comprised of two elements which are adjustably coupled together, generally along the craniocaudal axis, further ensuring that a secure fit around the spinous process is achieved.

The third feature of the Spinofacet stabilizer is an elongated rod-like connecting element. This feature may represent a separate element which is adjustably coupled to the Spinous Anchor as well as the as the Facet Anchoring Element, said coupling causing the Spinofacet stabilizer to provide fixation to the target motion segment in a unique, useful, novel and non-obvious fashion. However, in the preferred embodiment, this element actually represents the coupling of elongated extensions of the Facet Anchoring Element and the Spinous Anchoring Element. It must, of course, be recalled that any other embodiments which can be envisioned by those skilled in the art are all included within the spirit and scope of the invention.

In the preferred embodiment, the leading end of the Facet Coupling Extension arises from and is ideally monolithic with the trailing end of the Facet Base. This Extension is also provided with a shaft and a trailing end, the shaft of which is directed medially and slightly superiorly.

The trailing end shall couple with the leading end of a similarly-configured extension arising from the Spinous Anchor. The configuration of this coupling is unique, useful, novel and nonobvious.

The trailing end of the extension arises from and is ideally monolithic with the one of the hemi-elliptical elements of the Spinous Anchor. This is then continuous with a shaft which terminates in the leading end of the Spinous Anchor Coupling Extension. The leading end then couples with the Facet Coupling Extension. When this is accomplished [presumably] bilaterally, the Spinofacet Stabilizer confers stability to the target motion segment.

The unique, useful, novel and nonobvious coupling of the trailing end of the Facet Anchor Extension with the leading end of the Spinous Anchor Extension is accomplished by providing the ends of said Extensions with a unique configuration in which these ends, as seen in a transverse perspective, are slightly oblate rather than perfectly round, and therefore longest in one diameter (be it vertically or horizontally) and shortest in the orthogonal axis. Furthermore, the outer surfaces of sides of the longest diameter are substantially roughened so as to promote a "cold weld," when interfacing with another roughened surface. The exterior surfaces of the sides corresponding to the shortest diameter are smooth. It must be noted that in the preferred embodiment, the diameters of the Extensions as well as the textures of their outer surfaces should be parallel, although other configurations can be envisioned, which are of course within the spirit and scope of the invention.

Furthermore, this coupling is accomplished by another independent element known as the Coupling Modulator. This element is irreversibly coupled to one of the free ends of the Extensions. This is substantially cylindrical in configuration, the external surface of which is provided with a mechanism, be it ridges, a thumbscrew, or any acceptable mechanism for rotating the Modulator; thus, it allows the operator to rotate the Modulator around the long axis two Extensions, which can be seen entering the [open] sides of the cylindrical-shaped Modulator. It can be seen that ultimately, the coupling of the two Extensions is, in fact, actually the result of the coupling of each of the free ends to the Modulator.

In the example set forth here, the Modulator is coupled with the Facet Coupling Extension; it is borne in mind that an embodiment in which the Modulator is coupled to the Spinous Anchor Extension, as well as embodiments in which the Modulator is a completely independent element which is placed at the time of assembly are all incorporated into the Spirit and Scope of this disclosure.

The Modulator is a cylinder with a central channel passing therethrough, and apertures at each end which are continuous with said channel. The Modulator is irreversibly coupled to an extension by providing a slight enlargement of the circumference of the trailing end of the Extension at a point just beyond the aperture of the Modulator through which the shaft and trailing end of the extension are disposed. The geometry of this configuration is such that it permits free rotation of the Modulator but does not permit dislodgement thereof.

It can be understood that while the Modulator is irreversibly secured to one Extension, the other Extension can be disposed through the corresponding aperture such that the free ends of both Extensions are then housed within the channel of the Modulator. Again, in the example set forth, the leading end of the Spinous Anchor Extension would be free to be disposed into the channel of the Modulator.

As a practical matter, upon passing the free end of the Spinous Anchor into the Modulator, the surgeon or operator can then either distract or compress the target motion segment. This is a unique aspect of the invention when compared to any facet fixation systems which are currently on the market or in development.+

Once the motion segment has been adjusted to the desired craniocaudal dimension, the Spinofacet Stabilizer is locked in place. This is results from the coupling of the two Extensions to the Modulator. As has been disclosed the free ends of the Extensions are provided with a unique geometry, as well as opposite sides in which the exteriors can participate in a cold weld. These features are critical to the desired coupling.

The interior surface of the central channel is also uniquely modified to participate in this coupling. This channel is also slightly oblate rather than perfectly circular. In the non-deployed position, the greatest diameter of the channel is parallel to the greatest diameter of the Extensions. Furthermore, the sides of the smallest diameter of the channel are roughened to engage in a cold weld, while the sides corresponding to the longest diameter are smooth. This is opposite of the arrangement seen in the Extensions, wherein the sides of the greater diameter are roughened. It is again emphasized that the choice of which diameter is longest in the Extensions as well as the channel is somewhat arbitrary, and any such combination of diameters of the Extensions and Channel are within the spirit and scope of the invention.

It can now be seen that in the non-deployed position, the longest diameters of the two Extensions as well as the longest diameter of the channel of the Modulator are aligned, and that the smooth surfaces of the channel are aligned with the roughened surfaces of the Extensions while the roughened surfaces of the Extensions are aligned with the smooth surfaces of the channel.

Moreover, it is noted that rotating the Modulator approximately 90° will result in a re-alignment of these surfaces and diameters, such that with such a rotation, the roughened surfaces of the Extensions as well as the channel are now enmeshed creating a cold weld. Furthermore, aligning the shortest diameter of the channel with the longest diameter of the Extensions will create a mechanical "pressure-fit" lock, providing additional security to this important coupling.

Implantation of the Invention

In the preferred embodiment, the Spinofacet Stabilizer is implanted through a single limited midline incision. This is created from the lower half of the more cranial target spinous process to the uppermost portion of spinous process of the inferior vertebra. Such an incision would expose enough bony landmarks to allow the surgeon to complete the procedure in an efficient manner, while limiting the amount of tissue trauma and injury. An additional advantage for patient, surgeon and staff is that such an approach would limit the amount of radiation that would necessarily be utilized during the procedure.

The fascial attachments to the spinous process are then taken down, and the fascia in the midline is opened between the two spinous processes. A monolithic, purpose-specific blunt probing instrument, known as the Sub-fascial Dissector, is then introduced, which is provided with a leading end, a shaft and a trailing end. The purpose of the sub-fascial dissector is to create a tract from the spinous process to the FPT complex which will accommodate and seat the Facet Anchor and Coupling Extension, which is the initial step in implantation.

The leading end of the Sub-fascial Dissector is conical in configuration, with a blunted leading most end. It is further provided with a small extension, the FPT finder, which arises from the bottom of the leading end and is oriented and directed orthogonal from the long axis of the leading end. This FPT finder would, in reality, be directed anteriorly when the instrument is being utilized.

The junction of the leading end with the shaft is curvilinear such that the leading end is directed 60-90° from the long axis of the shaft. The shaft is then continuous with the trailing end, which is provided with handgrips for use by the surgeon. The instrument may be fabricated from any material known or acceptable to the art.

The surgeon introduces the FPT finder to create a sub-fascial tract through the muscles attached to the lamina and the facet joint, as well as the posterior surface of the transverse process. It is anticipated that in the preferred embodiment the Spinofacet Stabilizer is attached and rests entirely outside of the periosteum, with minimal disturbance of the periosteum. This is to reduce any inflammatory response which might be precipitated by significant disruption of the periosteum.

Introducing the Sub-fascial Dissector initially with its leading end directed anteriorly, the curvilinear configuration allows the surgeon rotate the dissector such that once the leadingmost end approaches the medialmost aspect of the lamina of the more cranial vertebra, and in this way advance the leading end towards the FPT complex. Once rotated, as the Dissector is advanced laterally, the FPT finder will detect the presence of the bony lamina as well as the step-off created lateral to the facet joint. Once this has been dissected cleanly and a tract created, the Dissector is removed.

Examination of the preferred embodiment of the Facet Anchor reveals that the geometry created by the relationship of the Transverse Process Claw to the Facet Base dictates that implantation of the Facet Anchor can be accomplished by one of three methods: 1) The Anchor is introduced through an incision directly posterior to the FPT complex, and specifically the Anchor is introduced with the leading end of the Transverse Process Claw and the long axis of the Facet Base parallel to the cranial aspect of the transverse process and rotated into the desired position; 2) The Anchor is introduced from a direct posterior incision such that the Facet Base is brought against the FPT complex and into its desired position, with the Transverse Claw initially in a non-deployed position parallel to the cranial edge of the transverse process, and then the Claw is rotated into the final desired position, or 3) The Anchor is introduced at a bias to its final desired position, and then the Anchor is rotated into the final desired position. This last approach could be undertaken from either a direct posterior incision, or using a single midline incision as being described herein. However, those familiar with the art may envision other strategies which can be used to introduce the Facet Anchor; all such embodiments are included within the spirit and scope of this application.

At this point, a unique, useful, novel and nonobvious instrument hereinafter referred to as the Facet Anchor Securing instrument is introduced. This instrument is provided with a leading end, a shaft and a trailing end. The instrument is to be fabricated from titanium, stainless steel, plastic, or any other substance known or acceptable to the art. The trailing end is a straight component which is a handle used by the surgeon to manipulate the instrument and thereby position the Facet Anchor in place; the trailing end of the instrument is also used to actuate the Securing Instrument at the time of implantation of the Facet Anchor. There is a curvilinear junctional area connecting the handle of the trailing end with the shaft. It is this curvature that allows the surgeon to direct, through a midline incision, the unique leading edge to implant the Facet Anchor into a more lateral position. This leading end has a somewhat blunted, cone-shaped leading most end which further dissects the soft tissues (muscle, tendons, ligaments, etc.) in preparation for the placement of the Facet Anchor.

The leading end is provided with a cradle which is configured to reversibly couple with the Facet Anchor and house it while the Securing Instrument is disposed through the soft tissues posterior to the vertebral column. This cradle maintains the Facet Anchor oriented to achieve its final desired position.

Several methods for actuating this instrument can be envisioned. Additional methods which may be anticipated by those familiar with the art would, of course, be included in the spirit and scope of this application. One such preferred method is achieved by providing the leading end of the instrument with a series of inflatable bladders which are pneumatically or hydraulically driven. The desired medium is transferred to the bladders via a series of tubes I channels which extend throughout the length of the Securing Instrument. At the trailing end, access portals to these tubes I channels provide the surgeon control over these bladders.

With inflation of the actuating bladders, the Anchor is held in a position biased to the final desired position, with the leading end of the Transverse Process Claw being held somewhat cranially and posteriorly to its final desired position. Upon positioning the Anchor within the leading end of the Securing Instrument, the surgeon then disposes the instrument through the tract which was created by the Subfascial Dissector. The leading end and shaft of the Securing Instrument are narrowed in comparison to the expanded leading end in which the Anchor is secured. With this configuration, the surgeon can tactilely identify the facet joint and the depression containing the FPT complex lateral to the facet joint. In an alternative embodiment, the Securing Instrument is positioned initially without the Facet Anchor secured into the leading end of the Instrument. In this embodiment, the trailing end and shaft have a central channel through which the Facet Anchor can be disposed, and then brought into final position by actuation of the leading end.

Upon identifying FPT complex, the instrument is further actuated by deploying and filling actuating bladders that are strategically positioned within the leading end of the Securing Instrument. With inflation of these bladders, the Facet Anchor is rotated around the base of the transverse process, and into position for final deployment. This rotation compels the Transverse Process Claw to now be anterior to the anterior surface of the transverse process, and in position to be brought against the TP/P surface; the Facet Base has now been brought against the FPT. The final set of bladders is now deployed, resulting in rotation of the Transverse Process Claw against the TP/P surface, and compressing the Facet Base firmly against the FPT complex. This locks the Facet Anchor into final position; the combination of these two actions results in the Facet Anchor becoming "cinched" against the posterolateral aspect of the target vertebra. It is to be recalled that barring special circumstances determined by the surgeon, this would routinely be performed bilaterally. At that point, the Securing Instrument can be removed.

It is critical that the trailing end of the Facet Anchor, which is in reality the trailing end of the Coupling Extension, remain easily identified rather than becoming completely covered over with soft tissues, resulting in difficulty in finding when the time comes for coupling with the Spinous Anchor. Therefore, an instrument known as the Spinofacet Locking Instrument is provided. This instrument is also provided with a leading end, a central portion, and a trailing end, and serves two functions: it makes the trailing end of the Facet Extension easily presentable for coupling with the leading end of the Extension arising from the Spinous Anchor; additionally, the Locking Instrument reversibly couples with the Coupling Modulator and allows the surgeon to lock the coupling of the two extensions.

The leading end of the Locking Instrument is provided with a configuration which will interface with the exterior surface of the Coupling Modulator, such that it can be left in the "non-deployed," setting while the Spinous Anchor is being implanted. In this way, it is easily identified when coupling the extensions is desired. Once the surgeon is satisfied with the position of the Spinofacet Stabilizer as well as the degree of distraction I compression of the vertebrae, the surgeon actuates the Locking Instrument which in turn rotates the Coupling Modulator which locks the two Coupling Extensions in place The central portion of the Locking Instrument is, in the preferred embodiment, provided with an approximately 90° curvature. This would allow the leading end of the instrument to be placed on the Coupling Modulator at the moment of the removal of the Facet Anchor Securing Instrument so that the trailing end of the Facet Extension does not become obscured by soft tissues; furthermore, the trailing end of the Locking Instrument could be laid against the skin, thus being kept out of the way until it is time to secure the Coupling Modulator. The trailing end provides the surgeon with a handle for placing and removing the instrument.

The next step in the insertion is to again utilize a blunt dissector which is purpose specific and known as the Spinous Process Dissector. This instrument is provided with a trailing end from which the device can be actuated. A central portion of the instrument then connects the trailing end with the leading end, which is provided with dual prong-like extensions which are used to create tracts through the soft tissues which will then accept the hemi-ovular shaped components of the Spinous Anchor.

The two halves of the Spinous Anchor are then inserted with the assistance of another unique, purpose-specific instrument, the Spinous Anchor Inserter. This instrument is provided with two separate leading ends which, in the preferred embodiment, are reversibly coupled to a central portion. The central portion is provided with two extensions which couple with the leading ends and which, in turn, are monolithic with a trailing end. The central portion of each extension is irreversibly coupled to its fellow by a pivot bolt which creates a scissoring configuration which is actuated by deploying the trailing end; this configuration is essential to the implantation of the Spinous Anchor.

The leading end of each half is further provided with a cradle by which it can reversibly couple with one of the hemi-ovular elements of the Spinous Anchor. The cradles are provided with a release mechanism such that once the Spinous Anchor is implanted, the cradles will be released from the hemi-ovular elements. Additionally, another unique feature of the Inserter is a pivotable joint at the junction of the leading end with the central shaft. This creates a situation which is ergonomically favorable insofar that the components of the Spinous Anchor can be disposed through the skin incision with their long axis orthogonal to the skin, and then this pivotable mechanism is deployed, rotating the components 90° so they can then be fitted into the proper position against the spinous process.

The central portion connects the leading ends to the trailing ends, and provides the important pivoting mechanism needed for the function of the instrument. The trailing mechanism is provided with handles by which the instrument can be deployed.

Deployment of this instrument involves mounting the two halves of the Spinous Anchor on to the two, separate leading ends of the Inserter. The importance that the leading ends of the Inserter are separate elements arises from the fact that each half of the Spinous Anchor includes a Coupling Extension; these extensions be initially coupled (but not locked in final position) with the Coupling Extensions of the Facet Anchor. This is most easily accomplished, from a mechanical perspective, prior to uniting the halves of the Spinous Anchor. Therefore, each half of the Spinous Anchor is coupled with a leading end of the inserter, disposed through the minimal incision and the two Coupling extensions are coupled within the Coupling Modulators. At this point, the Coupling Modulator remains in the non-deployed position.

Once the two Coupling Extensions of the Spinous Anchors are ideally in apposition with the trailing end of the Facet Anchors, the Coupling Extensions are coupled by deployment of the modulator. At that point, the independent leading ends of the Spinous Anchor Inserters are coupled with the central portion.

Upon this action, the two halves of the Spinous Anchor are now positioned in close apposition with each other. Deployment of the trailing end of the Spinous Anchor inserter results. The exact configuration of the leading ends places and maintains the two halves of the Spinous Anchor astride the spinous process, in the position necessary for the two halves to couple and form the Spinous Anchor. This is accomplished by a configuration in which the junctions of the leading ends and central portions of the Inserter are provided with an approximately 90° angle. This allows the Inserter to negotiate the components of the Spinous Process Anchor into position through a minimal incision.

In the preferred embodiment, the junctions of the central portions with the trailing ends are also monolithic, and again provided with an approximately 90° angulation. This is to provide the surgeon with an optimal ergonomic advantage during implantation. With this configuration, deploying the scissoring action of the Inserter allows the two halves to be brought together. Furthermore, the scissoring action of the Inserter allows the two halves of the Spinous Anchor to be compressed towards each other, thus actuating the ratcheting mechanisms of the components of the Spinous Anchor, ultimately resulting in a secure fit around the base of the spinous process. Such a fit is necessary in order to achieve the desired stability of the Spinofacet Stabilizer, and to create the unique, useful, novel and nonobvious spinal stabilization method herein disclosed.

Additionally, in the preferred embodiment, each half of the Spinous Anchor are, m turn, composed of two elements which are ratchetably coupled with each other such that they can be compressed along the craniocaudal axis, thus further compressing the Spinous Anchor against the spinous process. This increased fit is advantageous inasmuch that this further contributes to the stability of the construct. In such an embodiment, the Spinous Anchor Inserter is provided with a configuration which will allow actuation I deployment of the Inserter leading to compression of the halves of the Spinous Anchor in a craniocaudal direction.

As a final step in the implantation process, distraction or compression of the target motion segment must be established. This is done prior to deploying the Coupling Modulator, which would securely lock the Coupling Extensions, conferring the desired stability to the entire construct. Distraction or compression is established by yet another purpose—specific instrument, which is configured to interface with the Spinous Anchor as well as the Coupling Modulator.

In this embodiment, the bilateral Coupling Modulators will reversibly couple with the bilateral leading ends of the Vertical Adjuster, which is substantially "V" shaped, with the apex of the V reversibly coupling with the spinous process and I or the Spinous Anchor. Arising from this central element are the aforementioned adjustable arms. Once coupled with the Coupling Modulators, the arms can be further extended, leading to distraction of the motion segment. Alternatively, these arms can be retracted, thus leading to compression of the segment. This maneuver completes implantation of the invention.

It should be noted that in situations where extensive distraction or compression is desired, it may be necessary to provide trailing ends of the Facet Anchors, and possibly the trailing end of the Spinous Anchors, with a swiveling mechanism to allow for the change in the orientation of the connecting elements bilaterally precipitated by change in orientation of the Anchor elements with respect to each other after a significant distraction or compression. Such a mechanism can be envisioned as swiveling on a peg or similar structure connected to the central portion of the Facet Base. Clearly, it would also be necessary to be able to reversibly lock such a swiveling mechanism once the desired position is achieved.

Alternate Embodiments

One can envision multiple alternative embodiments of the invention; the most obvious of these are disclosed herein. It is to be recalled that those skilled in and familiar with the art may envision and offer other embodiments; such embodiments are also, be reference, included within the spirit and scope of the invention.

The first alternative embodiment disclosed herein addresses the issue of application of a Spinofacet Stabilizer to the L5-S1 segment. A moment's reflection will reveal that as there is no transverse process associated with the first Sacral segment, a significant alteration of the Facet Anchor will be necessary in order to utilize the device at this [most caudal] motion segment.

The inventor anticipates an embodiment in which a semicircular I hemi-ovoidal base can be brought against the cranial edge of the alar wings of the sacrum. It is expected that this base can be pressure fitted against the sacrum; an adjustable mechanism can be incorporated into the base for an even more secure fit against the sacrum. This base is then connected through an adjustable rod (as disclosed below) to the Spinous Anchor which would be secured to the L5 spinous process. This embodiment would likely be most useful in cases where distraction of the motion segment is desired.

In another embodiment of applying the invention to the L5-S1 motion segment, a curved bracket is passed along the caudal border of the superior facet process of S1. At that point, the two anchoring elements are distracted slightly. This distraction will then fixate the curved bracket against the S1 superior facet process.

Another alternative embodiment is disclosed for use at multiple levels. Obviously, one could merely apply individual Spinofacet Stabilizers to the target levels, achieving the desired result.

A Spinofacet Stabilizer can be specifically designed for application to multiple levels. In this embodiment, the multiple Spinous Anchors are connected by a bridging element.

Another aspect of this invention which can be achieved by multiple alternative embodiments is the coupling of the Transverse Claw to the Facet Base. In the preferred embodiment it can be recalled that the Claw I Base complex is initially implanted with the Claw oriented parallel to the long axis of the transverse process, and then the complex is rotated so that the Claw is then anterior to the process. At that point the Claw is rotated into final position against the lateral aspect of the pedicle.

The Numerous alternatives which can be anticipated can be generally be differentiated according to the method by which the Claw is brought against its target bony area, as well as the coupling of the Claw to the Facet Base.

Finally, the method of implanting the Facet anchors can vary. In general, this could be anticipated to include the preferred method disclosed above, utilizing a single midline incision in concert with an insertion instrument which passes the Facet Anchor into its initial position and then actuates the final positioning of the anchor element, including the positioning of the Transverse Claw.

Alternatively, the Spinofacet Stabilizer could be implanted through a minimal midline incision, as well as two small incisions centered over the facet complexes bilaterally. In this implantation approach, it is anticipated that initially, after accomplishing the aforementioned incisions, implantation cannulae would be bilaterally disposed through the lateral skin incisions and brought against the target bony area of the FPT complex. Then, the Facet Anchors would be disposed through the cannulae; it is anticipated that with this approach, it would be technically easier to manipulate the Facet Anchor, and a variety of approaches could be utilized in order to lock the Transverse Claw against the target bony area.

For instance, in one embodiment, the Claw is attached to the Facet Base in such a way that upon initial implantation, the long axis of the Claw is parallel to the long axis of the transverse process. Once the Facet Base has been brought securely against the FPT complex, the Claw is first rotated (approximately 90°) so that its long axis is (in its final position) orthogonal to the long axis of the transverse process, with the Claw anterior to the transverse process at its junction with the lateral aspect of the pedicle. At the point, the Claw is slidably repositioned along an anterior-posterior axis (In the transaxial view this would appear to be "up" and "down") such that the Claw can be securely brought against the target bony areas.

In yet another embodiment of the Facet Anchor, the Facet Base and the shaft of the Transverse Claw are coupled at the lateralmost aspect of the anchor. The long axis of the Claw is, in this embodiment, parallel to the long [craniocaudal] aspect of the Facet base, such that the Claw does not require rotation into position. The Facet Anchor is implanted by approaching the FPT complex from superior to the cranial aspect of the transverse process, and positioned with the Facet Base against the FPT complex and the Claw anterior to the transverse process. At that point, using the coupling of its two components as a fulcrum, the Facet Base and the Transverse Claw are compressed towards each other to provide a secure fit against the target bony areas.

In yet another embodiment, the Transverse Claw is semicircular in configuration, and is contained within the body of the Facet Base in its non-deployed position. Implantation then proceeds initially with placement of the Facet Base against the target bony areas; once in position, the Transverse Claw is deployed by being rotated out of the body of the Facet Base and around the cranial edge of the transverse process, to be brought against the target bony area.

DETAILED DESCRIPTION OF THE DRAWINGS

Background views have been provided to identify and define anatomic structures as well as the anatomic relationships, which are critical in understanding the function of the invention as it is applied to the spine. In both the Background Figures and the Figures demonstrating the invention, the exemplary motion segment demonstrated is the L4-L5 level; however, it is understood that with minor anatomic variations, the example set forth herein could be applied to any motion segment from T2-T3 to L4-L5. L5-S1, of course, has a unique anatomic arrangement, and is discussed and demonstrated in "Alternative Embodiments."

Figure 1:
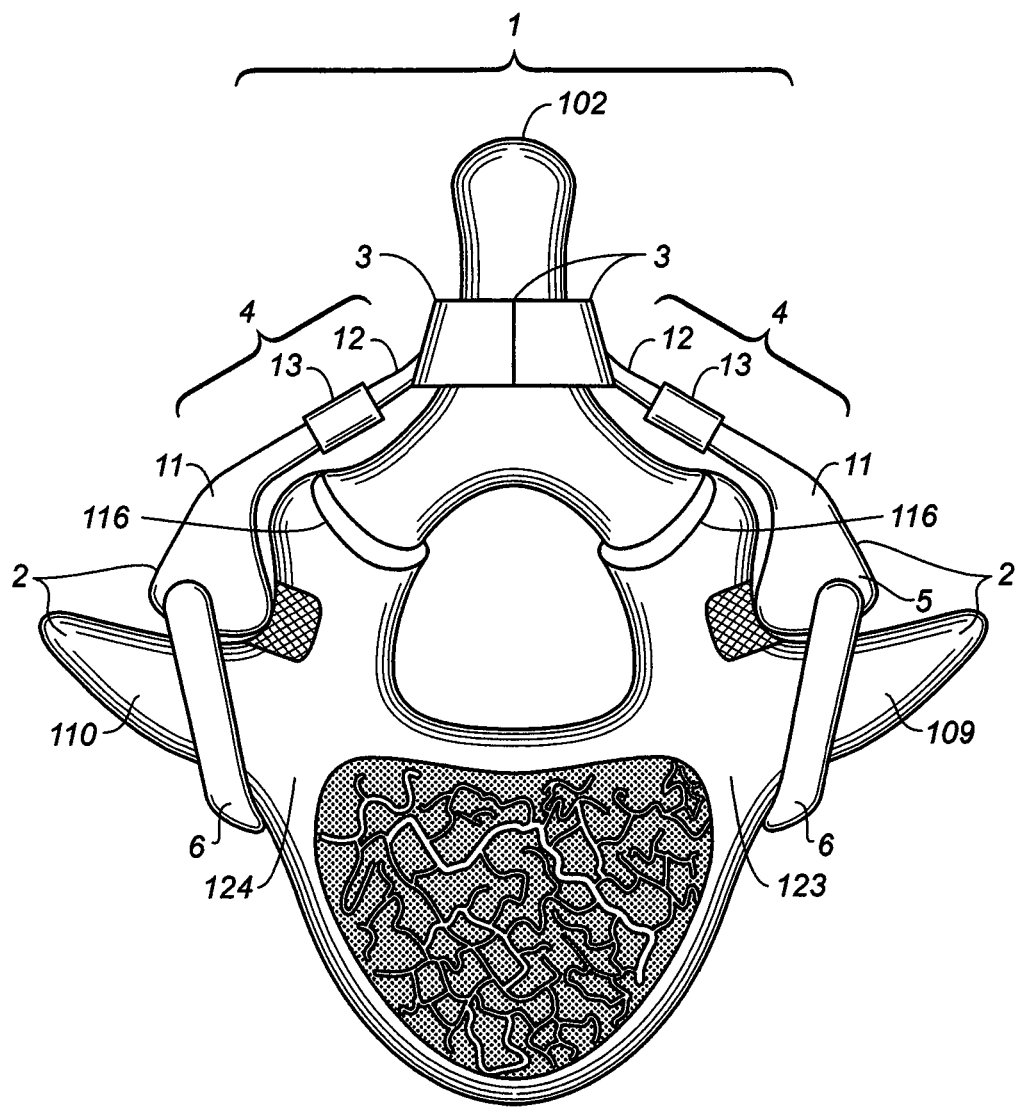
FIG. 1 is a frontal I transaxial view of the invention in place at L4-L5, with bilateral Facet Anchors in place on L5 and connected to a single, central Spinous Anchor (at L4)
Figure 22:
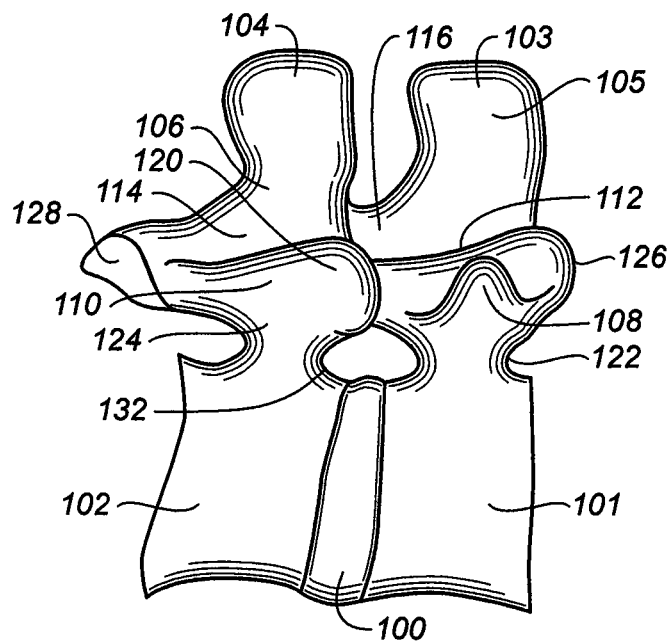
FIG. 22 is a posterior view of typical lumbar motion segment, in this case, L4-L5.

In FIG. 22, a posterior view of a typical L4-L5 motion segment has its natural anatomy demonstrated. The intervertebral disc 100 is not well seen in this posterior view as it is interpositioned between the upper L4 vertebral body 101 and the lower L5 vertebral body 102, both of which are also better appreciated in other views. The prominent midline structures are the spinous processes of L4 103 and L5 104, the tips of which are projected out towards the reader. The bases of these processes (105, 106) are better seen in the lateral view (Supplemental FIG. 2). Bilaterally projecting from the sides of the L4 vertebra is the left transverse processes 107 and the right transverse process 108. Similarly, at L5, the left and right transverse processes 109, 110 can be seen. This view best demonstrates the broad, flat laminae of both vertebrae, referring to L4 left-sided lamina 111 and right sided lamina 112, as well as L5 left and right, 113, 114; these plate-like structures form the "roof" or posterior aspect of the spinal canal, an effect which is best appreciated in the transaxial view I Supplemental image 3. Also seen in FIG. 1 is the posterior presentation of the zygoapophyseal joints, more commonly referred to as the facet joints 115 and 116—structures which are central to this disclosure. These joints are composed of the left and right inferior articular processes 117, 118, which are contributed by the upper or more cranial vertebra, and the left and right superior articular processes, which are contributed by the lower or more caudal vertebra. Pursuant to that arrangement, one can see the left 115 and right 116 L4-L5 facet joints, which are composed of the left 117 and right 118 L4 inferior articular processes, as well as the left 119 and right 120 L5 superior articular processes. The unarticulated L4 superior articular processes 125, 126 can be seen at the top of the motion segment, as can the unarticulated L5 inferior articular processes 127, 128. Importantly, it can be seen that the junctions of the Transverse Process with the Superior Articular Process presents a critical surface; this is the posteriormost portion of the pedicle (Best seen in the lateral perspective, Supplemental Image 2) and this area represents the FPT complex on the left 129 and right 130 [stippled areas], which are the sites against which the Facet Anchors will be brought.

Figure 23:
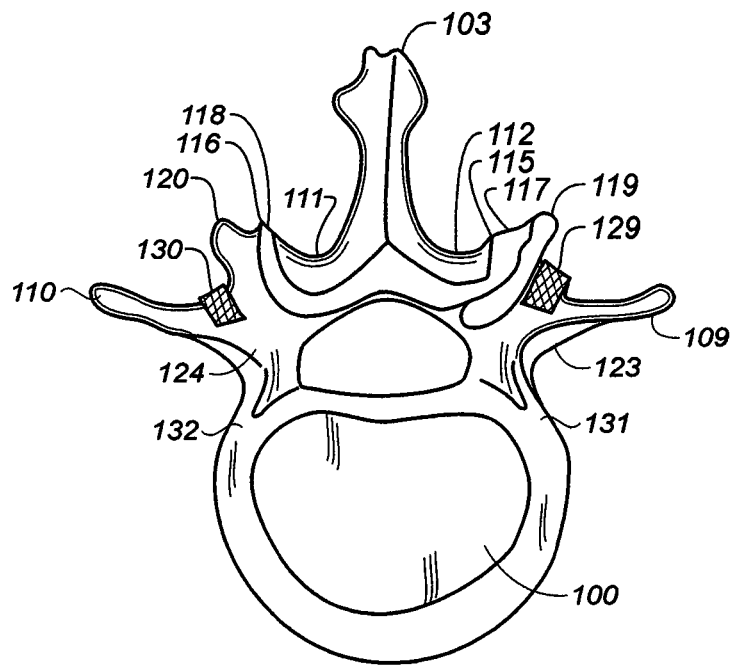
FIG. 23 is a lateral view of L4-L5 motion segment.

In FIG. 23, a lateral perspective of the right side of the L4-L5 motion segment, composed of the intervertebral disc 100, and several structures which could not be fully appreciated in the posterior view are now readily apparent. Most prominent of these is the large, anteriorly located Vertebral Bodies of L4 101 and L5 102. The right L4 Pedicle 122 and L5 Pedicle 124 are seen connecting the anterior Vertebral Bodies 101 and 102 to the posterior elements (the left sided L4 and L5 pedicles 121, 123 and the left neuroforamen 131 are not seen in this view). The opening between the right pedicles 122, 124 is the right L4-5 neuroforamen 132, from which the L4 nerve root (not demonstrated herein) would exit from the spinal canal. The right L4 Transverse Process (TP) 108 and L5 TP 110 can be seen projected The lateral aspects of the right L4-L5 facet joint 116, specifically the lateral aspect of the right L4 inferior facet process 122 as well as the right L5 superior articular process 124. The right-sided L4 and L5 laminae 112, 114 can be seen extending from the L4-5 facet complex 116 to join the base 105 of the L4 spinous process 103 and the base 106 of the L5 spinous process 104. Again, the unarticulated right sided superior articular process of L4 126 as well as the unarticulated inferior articular process of L5 128 are seen at the lateral extremes of the image. The stippled area is seen as the L5 FPT complex 130, where the facet anchor would be secured in a construct restraining this motion segment.

Figure 24:
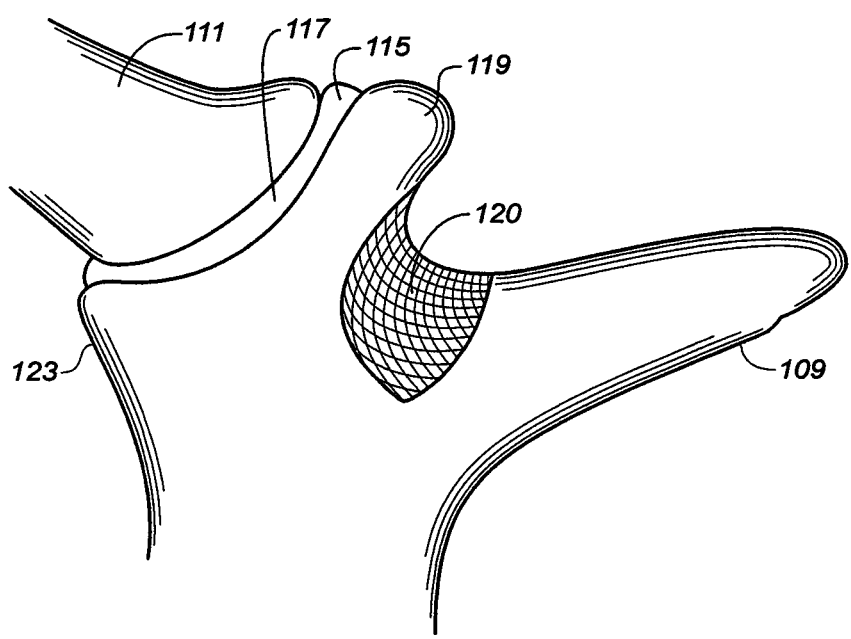
FIG. 24 is a transaxial view of L4-L5 motion segment.

In FIG. 24, a transaxial view, as seen from the cranial or superior perspective, at the level of the L4-5 disc space is seen. It is to be recognized that given this perspective, the subject's "left-sided" structures are portrayed on the viewer's right, and conversely, the subject's "right-sided" structures are portrayed on the viewer's left. This is the best view to understand how the laminae (in this case the left and right L4 laminae 111, 112) form the "roof," of the spinal canal. Surgeons often use the parlance "Unroofing the canal," when removing part or all of the lamina (i.e. "laminectomy,") to treat pathologies such as disc herniation and spinal stenosis, which affect intracanalicular structures such as the spinal cord, the cauda equina, and the nerve roots as the enter the neuroforaminal canals. In this case the left 131 and right 132 L4-5 neuroforaminal canals can be seen, although nerve roots are not demonstrated herein. The large rounded I ovoid intervertebral disc 100 is seen anteriorly, with the left 123 and right 124 L5 pedicles extending posteriorly, dividing into the left 119 and right 120 L5 superior facet processes and the left L5 109 and right 110 transverse processes. The pedicles can also be understood as connecting the vertebral body of L5 102 to the facet joints 115, 116, the laminae 113, 114 and the spinous process 104 (not well seen) of L5; collectively, this group of structures are referred to by functional anatomists as the "Posterior ring." The junction of the posterior aspect of the pedicles 123, 124, the transverse processes 109, 110 and the superior facet processes 123 and 124 together form the "FPT" complexes 129, 130 [stippled], which is the target for placement of the Facet Anchors. Also seen in this view is a transverse perspective of the L4-5 facet joints 116, 117, composed of the L4 inferior articular processes 118, 119 articulating with the L5 superior facet processes 120 and 121. The left 118 and right 119 L4 inferior articular processes are seen flowing into and continuous with the left 112 and right 113 L4 laminae, which then meet in the midline and form the base 105 of the L4 spinous process 103.

In FIG. 25: This transaxial view of the L4-5 facet joint as a representative joint recapitulates and further refines the anatomy of the facet joint illustrated in FIG. 23. In this image, the view is demonstrated from a cranial perspective, as this would offer a more detailed view of the anatomy which is anticipated to be the approach in implanting the Spinofacet Stabilizer. In this view, the lateralmost part of the left L4 lamina 112 is seen terminating in the left L4 inferior articular process 118. The terminal portion of the left L5 pedicle 130 is seen at the junction of the left L5 transverse process 110 with the left superior articular process 120, and this complex forms the FPT complex 135 against which the Facet Base portion of the Facet Anchor is brought.

DETAILED DESCRIPTIONS OF THE DRAWINGS DEMONSTRATING THE INVENTION

Referring now to the following drawings in which like numerals represent similar or identical elements throughout the several views, and referring particularly to FIG. 1, in which there is a frontal or transaxial perspective view demonstrating the L4-L5 motion segment onto which a Spinofacet Stabilizer 1 has been secured. It should be noted that throughout the drawings in this disclosure, the L4-L5 motion segment is used for a representative motion segment for demonstrative purposes; however, in fact this could represent any motion segment throughout the spine from T2-T3 to L4-L5. Facet Anchors 2 have been applied bilaterally, as is anticipated will be the case in the vast majority of instances. The three components of the Stabilizer device 1 are the Facet Anchoring Elements 2, which have been applied against the FPT complexes [stippled areas] of L5;

the Spinous Anchoring Element 3, which has been applied to the spinous process of L4 in this view, and is comprised of the left 15 and right 16 cranial quadrants; and the Connecting Elements 4. In this preferred embodiment illustrated here, the Connecting Elements 4 represent the coupling of the coupling extensions 12 of the Spinous Anchors 3 as they are reversibly coupled with the coupling modulator 13 on the coupling extensions 11 of the Facet Anchors. The Facet Anchors 2 are seen comprised of a Facet Bases 5, which are brought against the FPT complexes, and the Transverse Process Claws 6, which are brought against the junction of the transverse processes 109, 110 with the lateral aspects of the pedicles 123, 124. This point 14 is referred to in this disclosure are TP/Ped complex. Anatomic landmarks in this image also include the L5 vertebral body 102. It can be seen that the Facet Anchors 2 extend dorsally over the left 115 and right 116 facet joints, hence stabilizing them.

Figure 2:
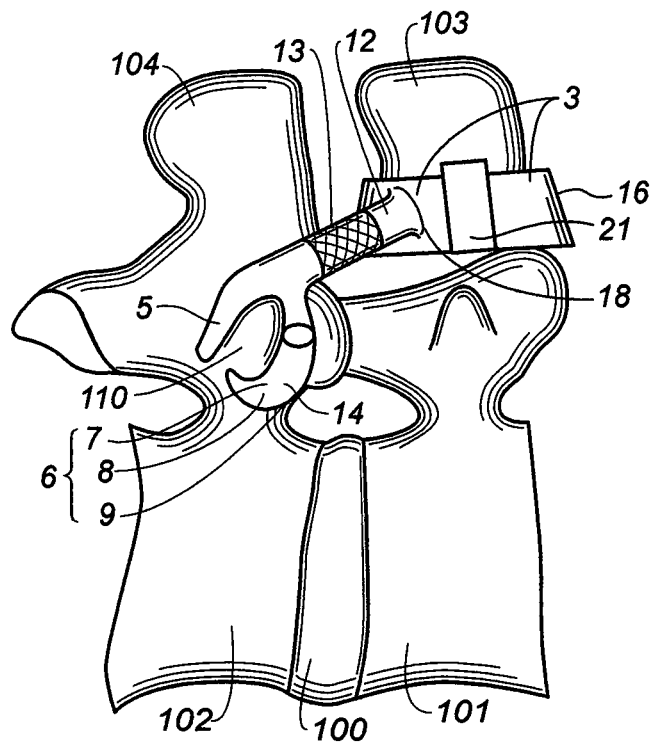
FIG. 2 is a right lateral view of the L4-L5 motion segment with the right side of the Spinofacet Stabilizer in position.

The stabilization established by the invention is further appreciated in FIG. 2, in which a right lateral view of an L4-L5 motion segment that has been stabilized with the Spinofacet Stabilizer, the Transverse Process Claws 6 are seen relating to the cranial aspect of the right L5 transverse process 110. The curvilinear leading end 7 of the Transverse Process Claw 6 is seen having been brought against the target bony surface area which is the transverse process I lateral pedicle junction 14. The shaft 8 is seen extending from the leading end 7 to the trailing end 9 of the Transverse Process Claw 6. The trailing end 9 couples with the cranial aspect of the Facet Base 5, which is in turn secured against the right L5 FPT complex (not seen in this projection) thus incorporating the L5 vertebra 102 into the construct created by the Spinofacet Stabilizer 1. The trailing end of the coupling extension of the Facet Anchor 11 is coupled with the Coupling Modulator 13, which is in turn coupled with the leading end of the coupling extension of the Spinous Anchor 12; the Spinous Anchor 3 is secured to the spinous process of L4 103, thus completing the construct. In this perspective, the Spinous Anchor can be seen as comprised of the right Cranial Spinous Quadrant 16 and the right Caudal Spinous Quadrant 17 which are adjustably connected by the right Lateral Spinous Coupler.

Figure 3:
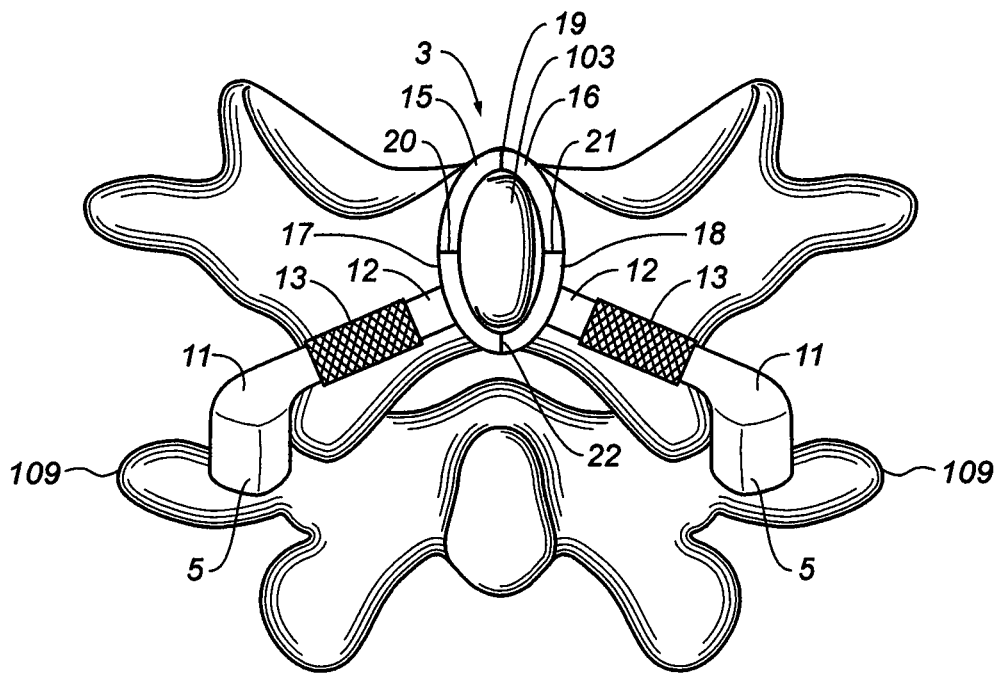
FIG. 3 is a posterior view of the L4-L5 motion segment after the application of the Spinofacet Stabilizer.

FIG. 3 allows for a greater understanding of the components of the Spinofacet Stabilizer 1 by providing a posterior view. Centrally, the Spinous Anchor 3 can be seen as composed of 4 elements which are adjustably assembled together to form an ovoid ring which can be tightly secured against the spinous process. These include the left 15 and right 16 cranial spinous quadrants, as well as the left 17 and right 18 caudal spinous quadrants. As demonstrated in this and other images, each of these components is coupled with two other components of the Spinous Anchor in the fashion illustrated. The coupling mechanism which is anticipated as the preferred method is a ratcheting mechanism, but that is not illustrated in this image; however, any method of adjustable coupling is included within the spirit and scope of this invention. It can be seen that at the most cranial aspects of the Spinous Anchor, the left 15 and right 16 cranial spinous quadrants are coupled by the cranial spinous coupler 19. The left cranial spinous quadrant 15 then also couples with the left caudal spinous quadrant 17 at the left lateral spinous coupler 20; in a similar manner, the right cranial spinous quadrant 16 couples with the right caudal spinous quadrant 18 through the right lateral spinous coupler 21. Finally, the caudal spinous coupler 22 couples the left 17 and right 18 caudal spinous quadrants. Providing the Spinous Anchor 3 with an adjustable coupling at all 4 points insures that the Anchor can be secured to the spinous process (not shown in this image) with adequate fixation so that there is no movement, which would reduce the fixation of the invention as a whole. Arising from the left 17 and right 18 caudal spinous quadrants are the left and right coupling extensions 12. Each of these then couples with the coupling modulator 13 on their respective sides. In the preferred embodiment, the coupling modulators 13 are coupled with the trailing ends of the coupling extensions 11 of the Facet bases 5. The Facet bases 5 are then coupled to the trailing end of the TP claws, as previously shown in FIG. 3. The transverse processes of L5 on the left 109 and right 110 are also labeled for orientation of the reader.

Figure 4:
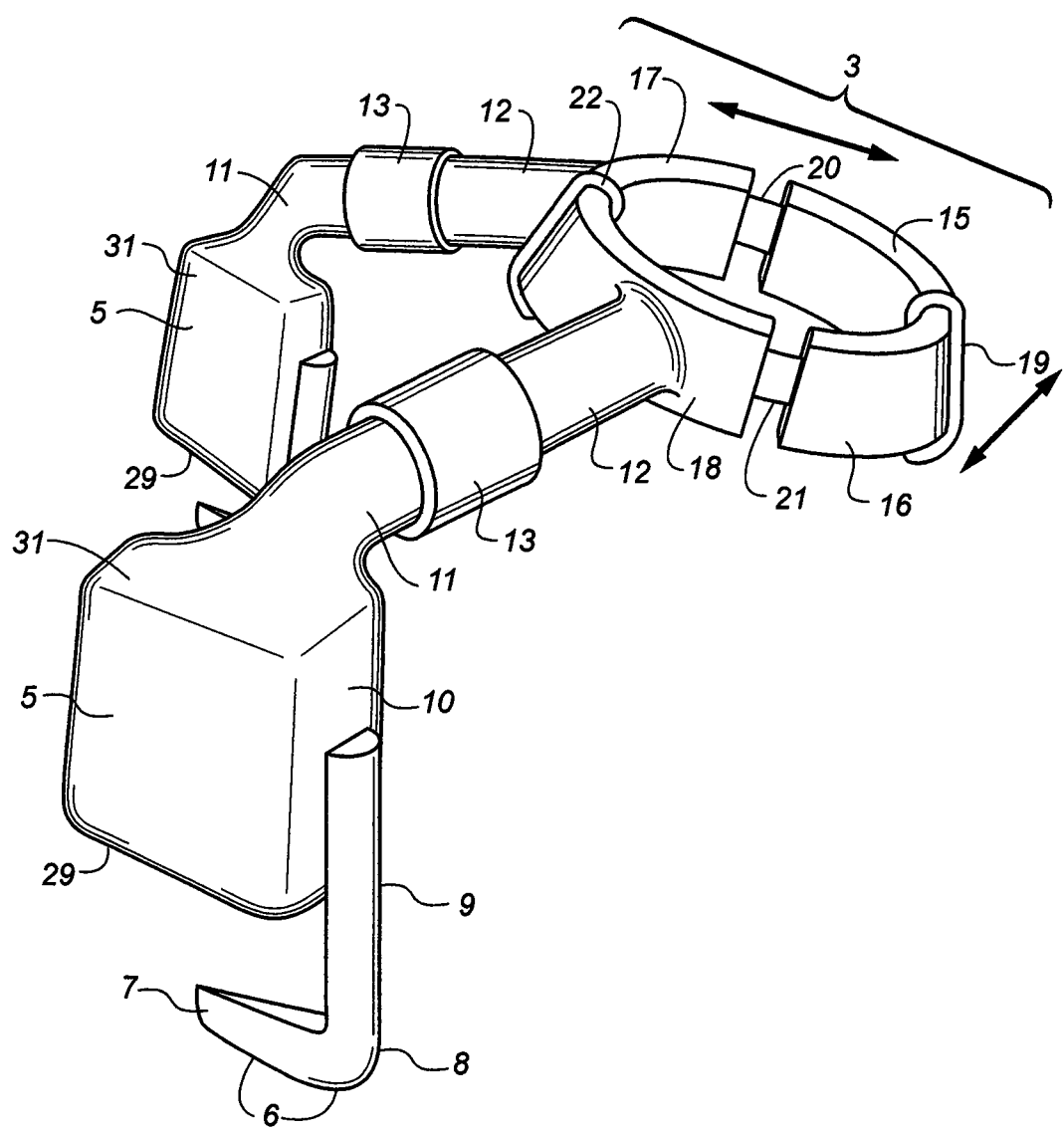
FIG. 4 is an elevational view of the Spinofacet Stabilizer from the right side.

An elevational view of the Spinofacet Stabilizer as seen from the right side allows FIG. 4 to demonstrate the structure of the invention in its entirety. The midline Spinous Anchor 3 is adjustable in both the craniocaudal and mediolateral axes, as demonstrated by the arrows, owing to the adjustable nature of the coupling of its component elements, the left and right Cranial Spinous Quadrants 15, 16 as well as the left and right Caudal Spinous Quadrants 17 and 18. As demonstrated in other views, this assures a secure fit onto the spinous process. The Cranial Quadrants are adjustably coupled by the Cranial Spinous Coupler 19. The left Cranial and Caudal Quadrants 15, 17 are coupled by the Left Lateral Spinous Coupler 20, and the right quadrants 16, 18 are similarly coupled by the Right Lateral Spinous Coupler 21. It then becomes apparent that the caudal quadrants are coupled by the Caudal Spinous Coupler 22. It can be further seen that the Coupling Extensions 12 of the Spinous Anchors 3 couple with the Coupling Modulators 13, which in turn couples with the Coupling Extension 11 of the Facet Anchors 2. More specifically, the Coupling Extensions 11 of the Facet Anchors 2 are then continuous with the Facet Bases 5, the leading ends 29 which have been brought against the FPT complexes to stabilize the facet joints and allow the Spinofacet Stabilizer 1 to either compress or distract the target motion segment. The cranial aspects 10 of the Facet Bases 5 couple with the Transverse Process Claws 6. This mechanism fixes the device against the posterior aspect of the target vertebra, thus stabilizing the construct.

Figure 5:
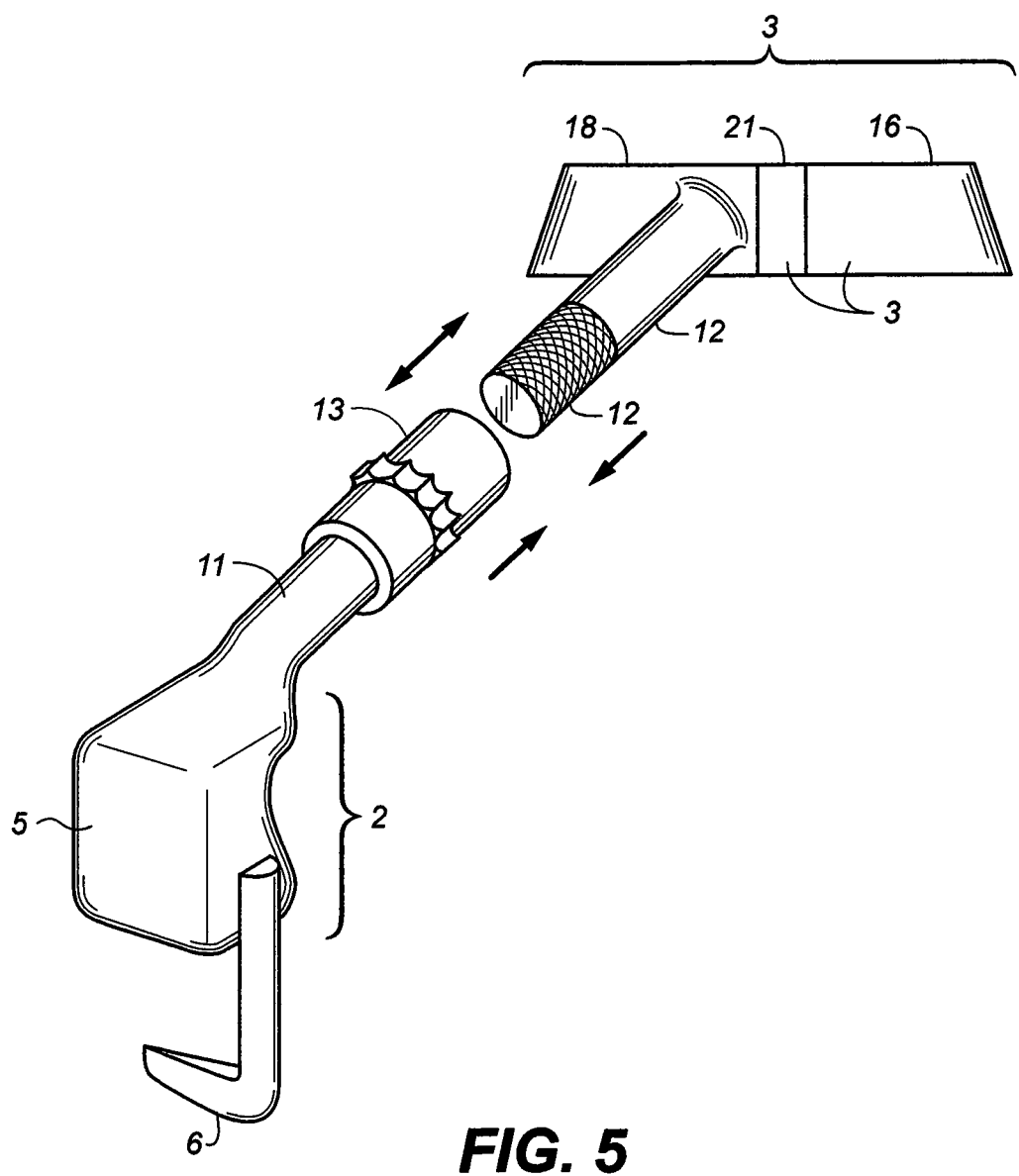
FIG. 5 is a right lateral view of the Spinofacet Stabilizer with the Facet and Spinous Anchors isolated.

In order to understand how the invention can result in either distraction or compression of the target motion segment, FIG. 5 shows a right-sided view of the invention, demonstrating the Spinous Anchor 3 securing the upper vertebra of the target motion segment while the Facet Anchor 2 is secured to the lower vertebra. The arrows demonstrate how the Coupling Extension 12 of the Spinous Anchor 3 can be inserted into the Coupling Modulator 13 and then the two anchoring elements can be moved closer together to result in compression, or pulled further apart resulting in distraction, in accordance with that action deemed necessary by the surgeon. The other structures seen in this view are the right Cranial and Caudal Spinous Quadrants 16, 18 the right lateral coupler 21. It is to be recalled that the Coupling Modulator 13 may be irreversibly coupled to either the Facet Coupling Extension 11 or the Spinous Coupling Extension 12.

Figure 6:
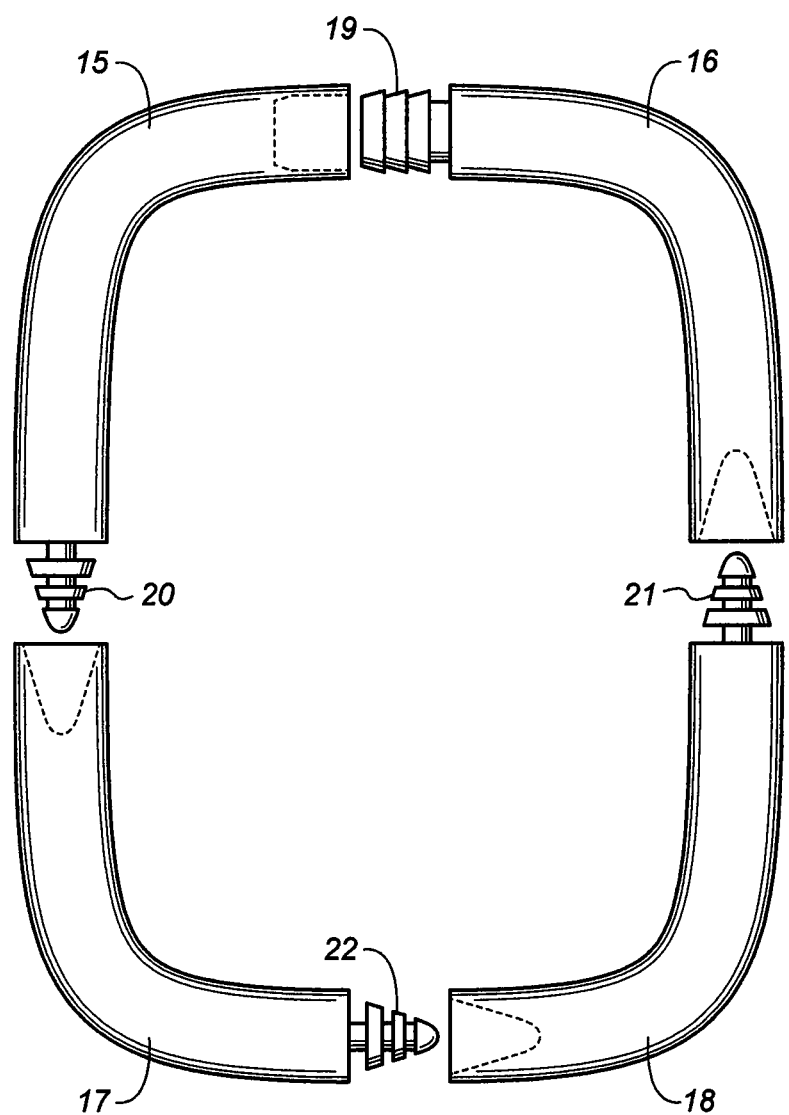
FIG. 6 is a posterior view of a disarticulated Spinous Anchor.

Demonstrating how the Spinous Anchor securely attaches against the surfaces of the spinous process, a top view of a disarticulated Spinous Anchor is provided in FIG. 6. This shows a preferred embodiment of 4 components, specifically the left 15 and right 16 cranial quadrants and the left 17 and right 18 caudal quadrants. These are coupled by the Cranial Spinous Coupler 19, the Left and Right Lateral Couplers 20, 21 and the Caudal Coupler 22. It is noted that various configurations of the coupling mechanism are portrayed herein, and it is known that other iterations could be identified and are keeping within the spirit and scope of the invention.

Figure 7:
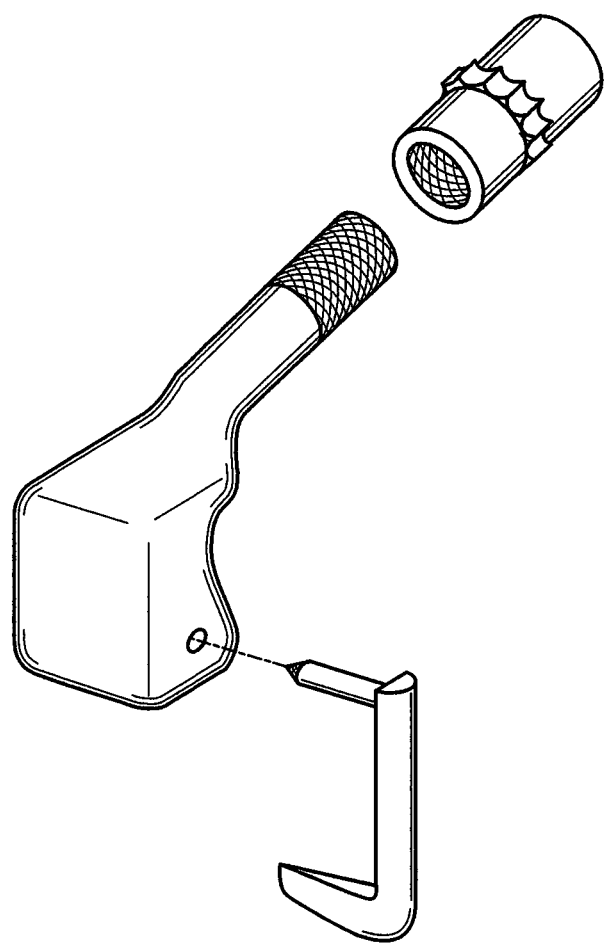
FIG. 7 is an elevational view of the Exploded Facet Anchor.

FIG. 7 is an elevational exploded view of the Facet Anchor 2. It can be seen that this component is comprised of two elements, the Facet Base 5 and the Transverse Process (TP) Claw 6. These two elements are coupled by the insertion of the coupling extension 26 of the trailing end 9 of the TP Claw into the insertion aperture 28 of the cranial side 10 of the Facet Base 5. This insertion is provided with a ratcheting mechanism or some other adjustable mechanism such that the Transverse Process Claw 6 can be rotated from the lateral to the medial perspective, and in this fashion achieve a secure locked fitting against target bony area. This is further important as this ratcheting mechanism will also provide a more secure fit of the Facet Anchor against the bone. The Facet Base 5, in turn, is provided with a leading end 29, a central portion 30, and a trailing end 31. The leading end is brought securely against the FTP complex, to maximize the grasp of the Facet Anchor. Also noted is the Coupling Extension 11 arising from the Trailing End 31 of the Facet Base 5. The trailing most end 32 of the Coupling Extension 11 is provided with a roughened surface, which when interfacing with the interior 27 of the Coupling Modulator results in a cold weld.

Figure 8:
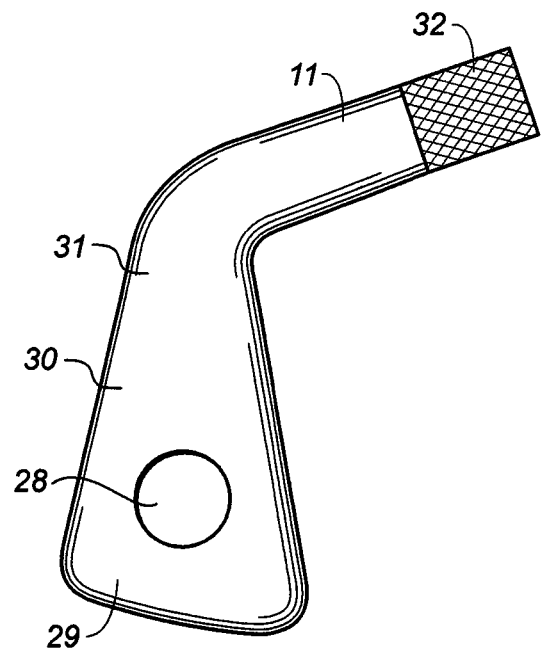
FIG. 8 is a lateral view of the cranial side of a Facet Base.

FIG. 8 further demonstrates the Facet Base 5. The leading end 29 is configured to achieve maximum apposition against the target bony surfaces, which ultimately results in greater efficiency of the invention. The Coupling Aperture 28 accepts the Coupling Extension of the Transverse Process Claw (not Shown); the interface therein results in the rotation of the Transverse Process Claw into acceptable position. Also shown here is the Central portion or Body 30 of the Facet Base 5, as well as the Trailing End 31, and the Coupling Extension 11. Again, the Trailing most end 32 of the Coupling Extension 11 is noted to be roughened in order to be secured into a cold weld.

Figure 9:
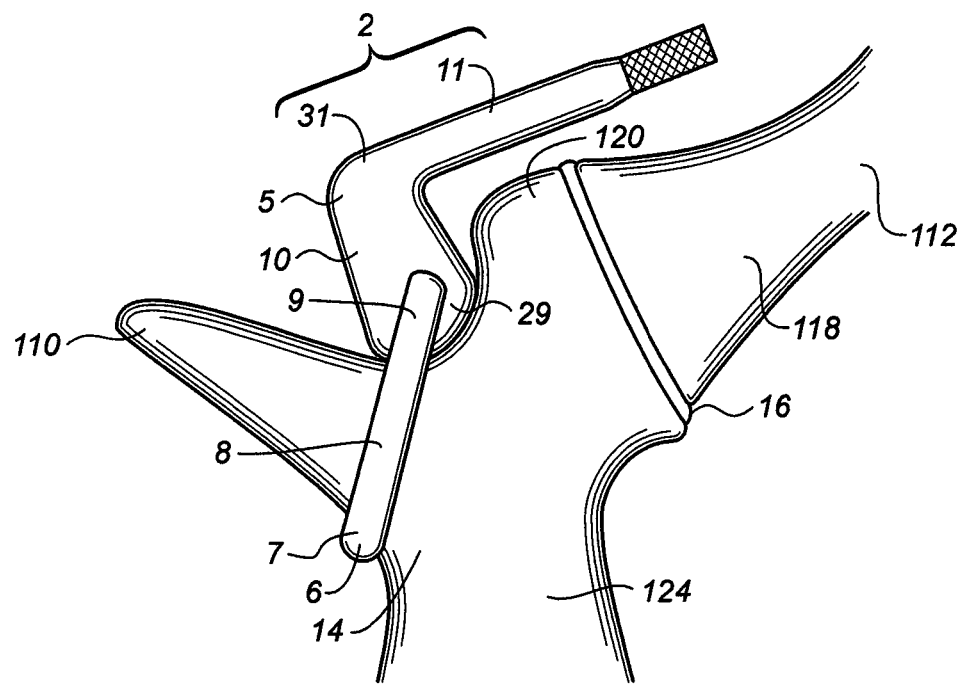
FIG. 9 is a transaxial view of the right L4-L5 facet joint with a Facet Anchor in Place.

FIG. 9 shows the Facet Anchor 2 in position as demonstrated in a transaxial perspective of a representative facet joint, in this case the L4-L5 right sided facet joint. The bony landmarks include the lateralmost aspect of the right L4 lamina 112, as it sweeps into and becomes the right L4 inferior articular process 118, and articulates through the right L4-5 facet joint proper 116 with the right L5 superior articular process 120. Also seen are the right L5 pedicle 124 and the right L5 transverse process 110. The leading end 7 of the Transverse Process Claw 6 as it is compressed against the TP/Ped complex 14. The shaft of the Transverse Process passes over the cranial aspect of the transverse process 110 to couple with the Cranial aspect 10 of the Facet Base 5. The Trailing End 31 of the Facet Base 5 is continuous with and monolithic with the Coupling Extension. As this is disposed over the Facet Joint 116, it stabilizes the joint.

Figure 10:
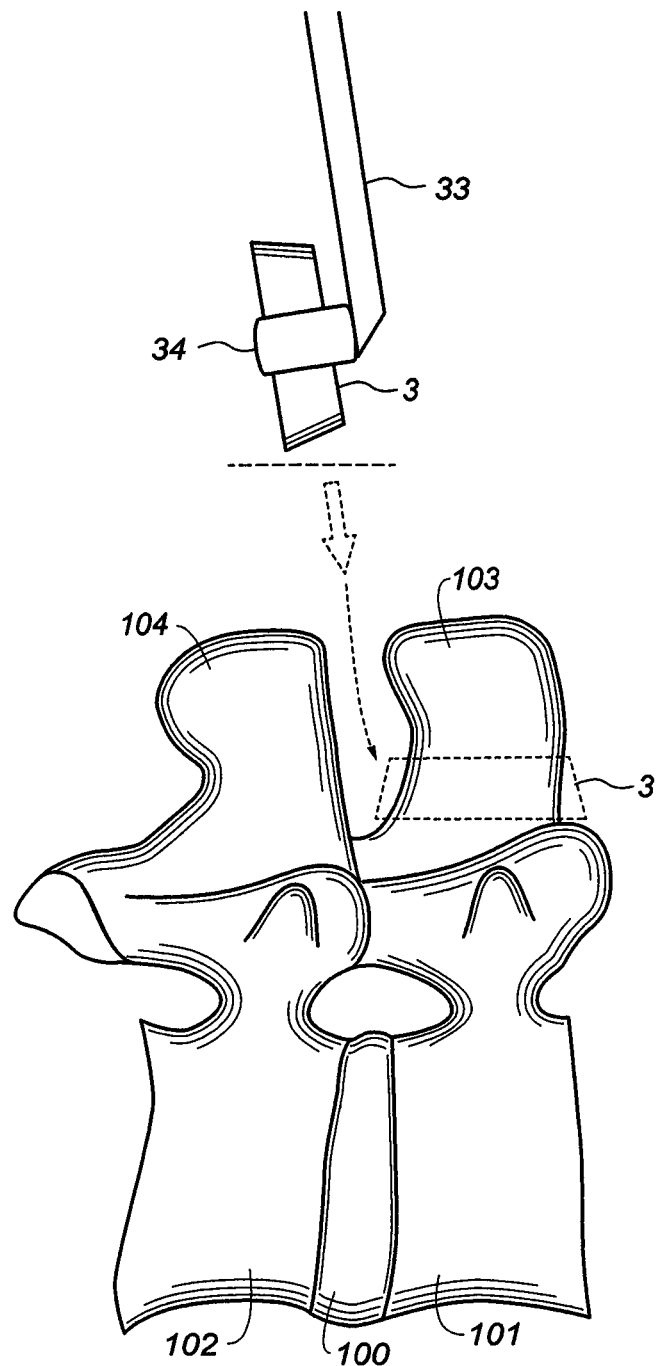
FIG. 10 is a lateral view of the L4-5 motion segment during the first phase of implantation.

FIG. 10 is a right lateral perspective of the L4-5 motion segment, with the L4-5 disc space 100, the L4 101, the L5 102 and the respective spinous processes 103, 104. This image demonstrates the process of implanting the invention. In the first step, after a skin incision is made (horizontal dotted line), and the Spinous Anchor insertion device 33 is used to dispose the Spinous Anchor 3 through the incision. It is noted that the initial incision is made with the Spinous Anchor orthogonal to its final orientation. Once it has been positioned between the L4 spinous process 103 and the L5 spinous process 104, the device is deployed, and the Spinous Anchor is rotated into its final orientation so that it can be compressed until the correct size is achieved.

Figure 11A:
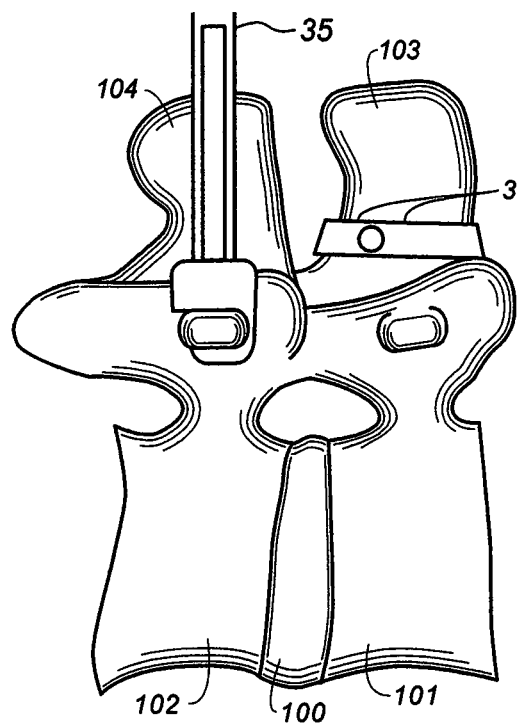
FIGS. 11A and B are lateral views of implantation of the Facet Anchor and connecting rod.
Figure 11B:
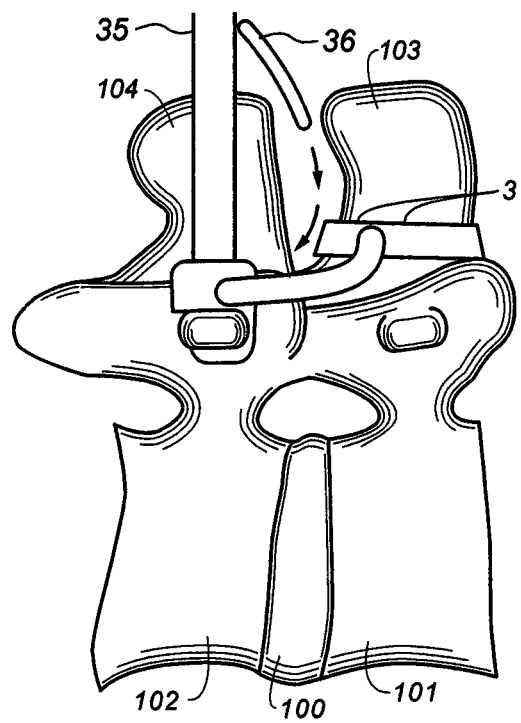

Once the Spinous Anchor is in place, one method for completing the implantation of the invention is to utilize the method described in FIG. 11A/B. In FIG. 11A, after implantation of the Spinous Anchor 3 on the L4 spinous process 103, an insertion cannula 35 is disposed through a tract and positioned against the FPT complex. The Facet Anchor is passed through the cannula, and the Facet Anchor is applied to the target bony surfaces. At that point, as demonstrated in FIG. 11B, a connecting rod element 4 is disposed through a submuscular tract until it is coupled with the Facet Anchor 2, and subsequently coupled with the Spinous Anchor 3. The right L4 140 and L5 141 are seen escaping from the spinal canal.

Figure 12A:
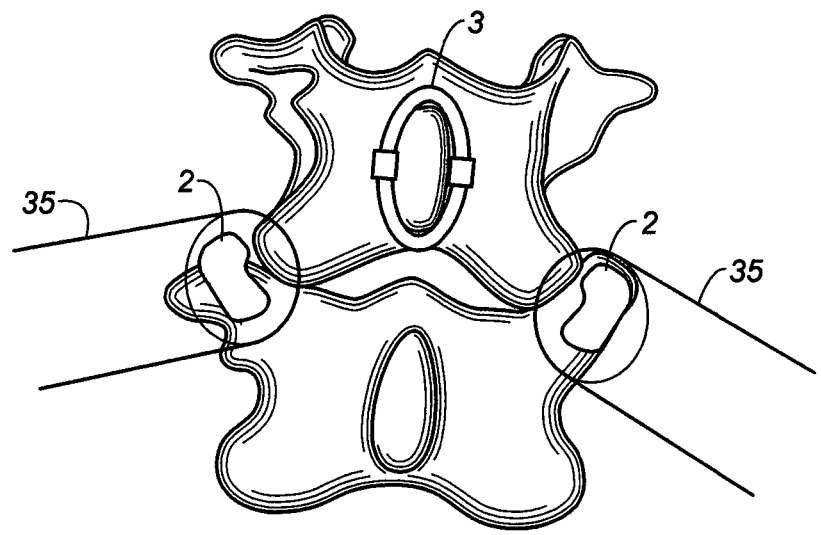
FIGS. 12A and B are posterior views of implantation of the Facet Anchor and connecting rod.
Figure 12B:
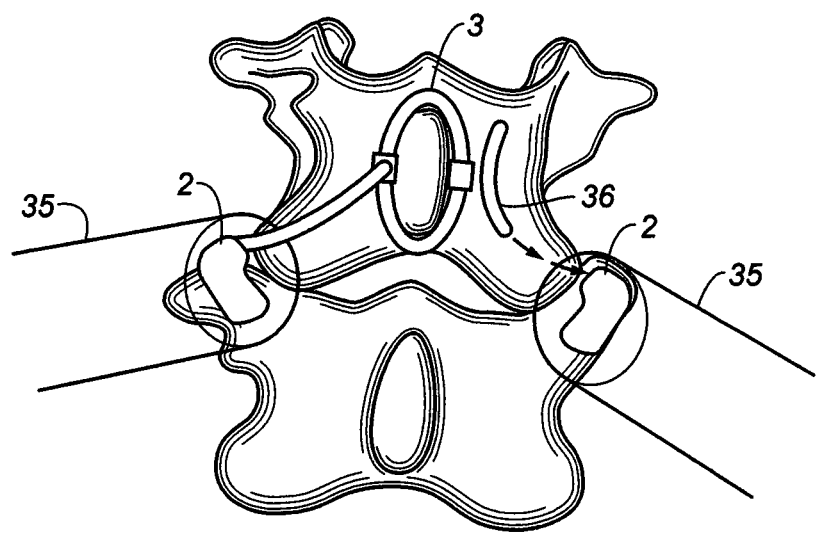

This process is again illuminated in FIGS. 12A/B. These images show a posterior view of the implantation procedure discussed in FIGS. 11A/B above. Again, the Spinous Anchor is initially implanted and secured, followed by placement of an implantation cannula 35 over the facet joint. The Facet Anchor 2 is then secured into place, and the Connecting rod 4 is passed between the two anchoring elements and secured to both.

Figure 13:
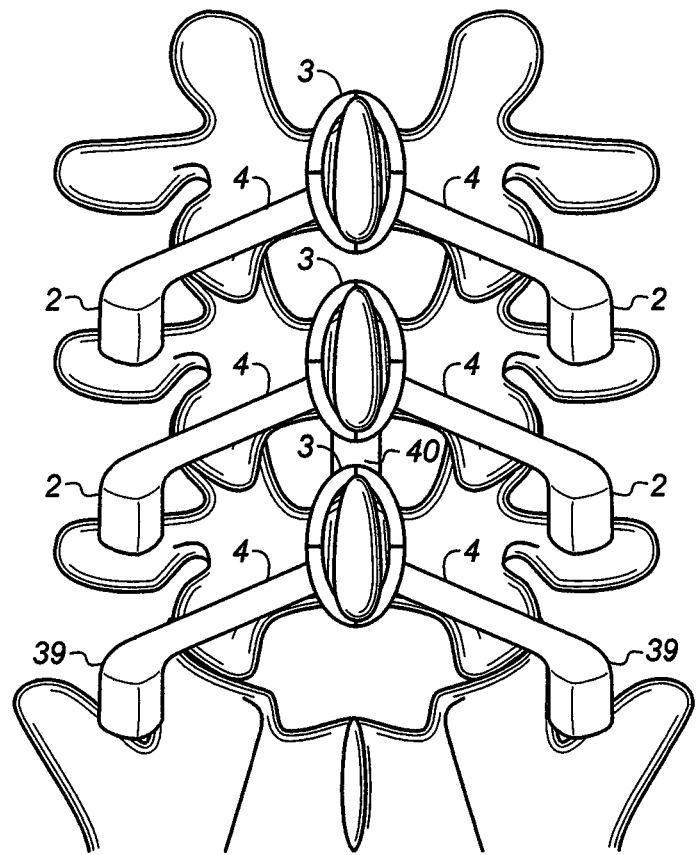
FIG. 13 is a posterior view of multi-level iteration of the invention.

FIG. 13 demonstrates the posterior view of a multi-level construct, in this case spanning from L3 to S1. At each level, the Spinous Anchor 3 is present, as well as the connecting element 4, and the Facet Anchor 5. Such a construct can be achieved with the use of either multiple independent Spinofacet Stabilizers, or a bridging element 40 can be introduced. In this construct, L5-S1 requires special variations, including the use of S1 sickles 41.

Figure 14:
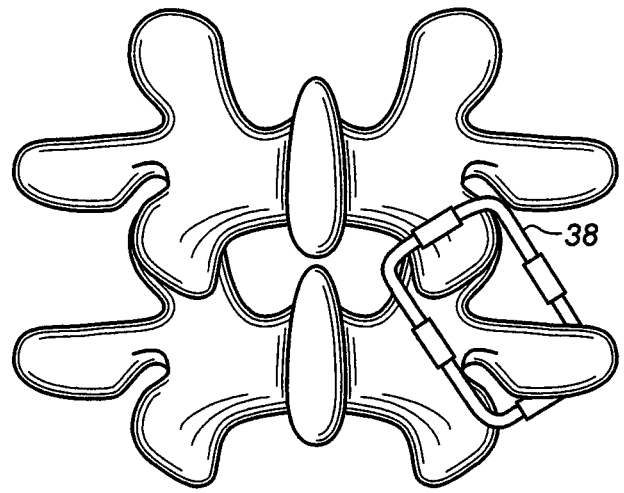
FIG. 14 is a posterior view of an alternative embodiment in which the spinous process is not used.

FIG. 14 shows the posterior view of an alternative embodiment, in which the Spinous Process is not incorporated into the stabilization scheme.

Figure 15:
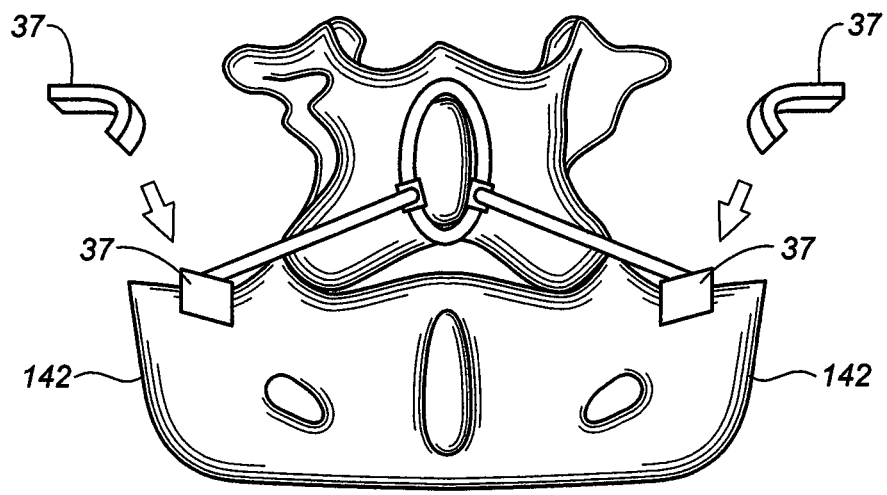
FIG. 15 is a posterior view of iteration stabilizing L5-S1.

FIG. 15 achieves stabilization at L5-S1. It is recognized that there is no transverse process present at S1, and a greatly reduced so that achieving stabilization requires alternative embodiments. In this embodiment, a Spinous Anchor 3 is placed at L5, as are connecting elements 4. A bracket/block 37 is passed over the sacral ala along its edge, and after achieving a reasonably secure fit this is coupled with the Connecting Element 4.

Figure 16:
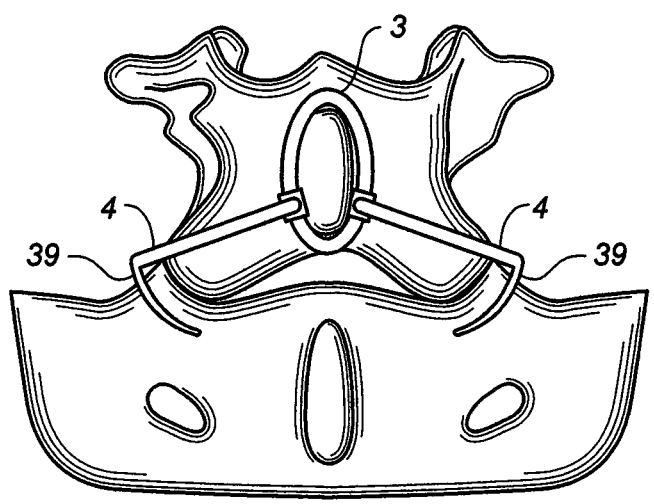
FIG. 16 is a posterior view of variation of L5-S1 stabilization.

FIG. 16 demonstrates a variation of the theme at S1, in which a sickle-shaped bracket is passed along the caudal edge of the S1 superior articular process 143, and after connecting this to the Spinous Anchor, a secure stabilization is achieved.

Figure 18:
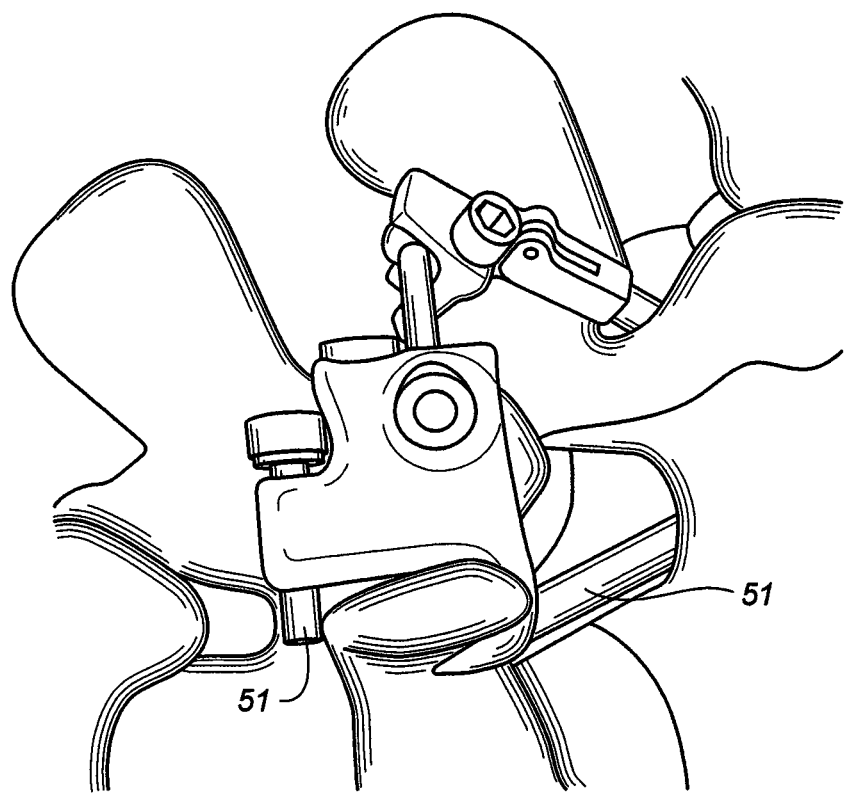
FIG. 18 shows the same embodiment as shown in FIG. 17, from the side.
Figure 19:
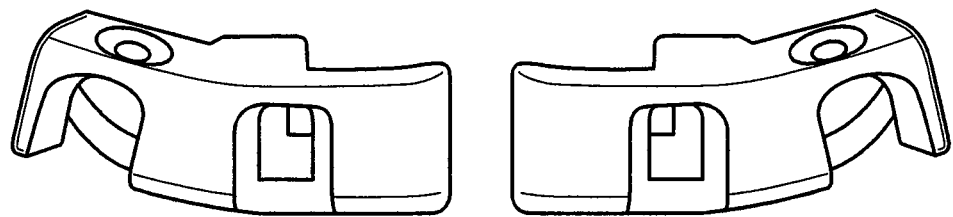
FIG. 19 shows an embodiment of the facet anchor base using a clamp 51 and a screw 52.

In FIG. 18 we see the facet base 45 includes a facet clamp portion 46 and an adjustable locking claw 47. The facet clamp portion and the locking clamp portion cooperate with each other to grip the facet process. The base also includes a socket 48 into which a rod-like extender 49 with a ball end 50 can be inserted through to form a lockable joint. The extender can be extended and rotated to the spinous anchor segment 44 in this embodiment.

Figure 17:
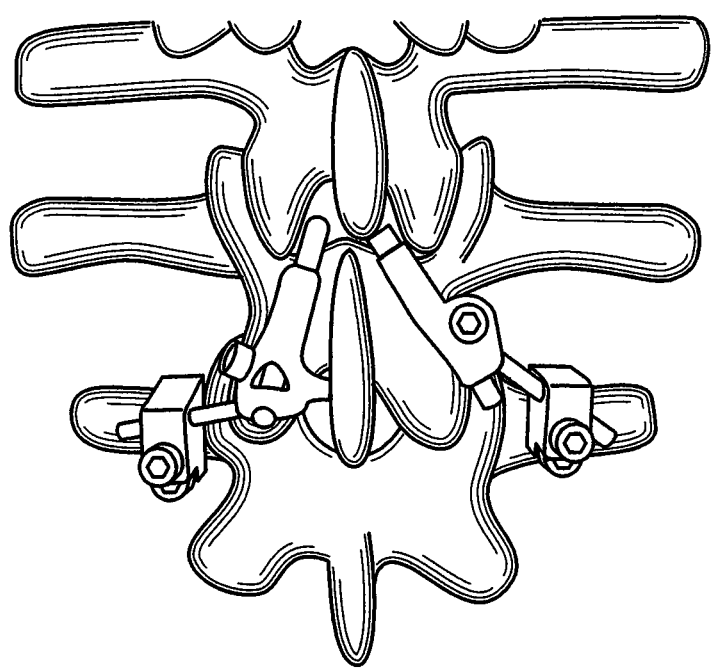
FIG. 17 shows an anterior view of an embodiment of the invention with two facet anchors 42, and 42a; two extensions 43 and 43a and two spinous anchor segments 44 and 44b.

FIG. 17 shows that the facet base anchors can be deployed in two different orientations allowing for a flexibility of use in application. The facet anchor bases can employ one clamp and a screw in an alternate embodiment to fix to the facet process. The facet can also be angled 53 to improve fit.

Figure 20:
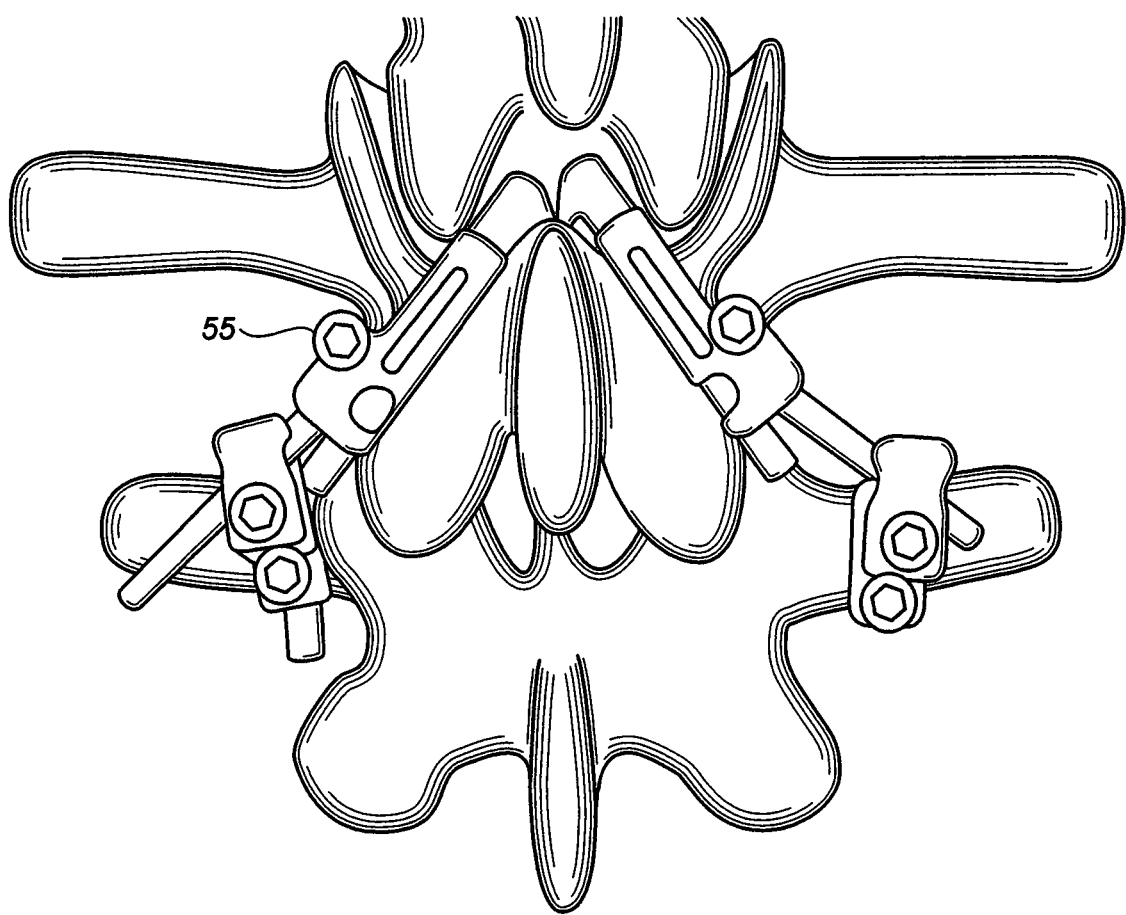
FIG. 20 illustrates another embodiment of the invention.
Figure 21:
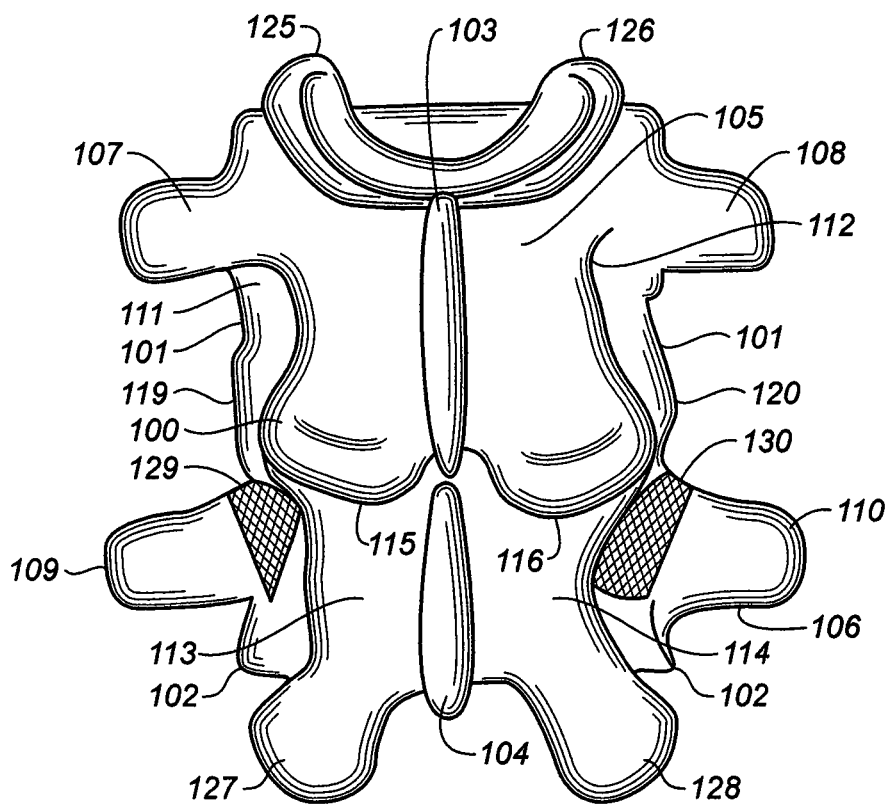
FIG. 21 illustrates the spinous anchor of the embodiment shown in FIG. 17.

In another embodiment of the invention FIG. 20 the spinous anchor comprises two separate portions each of which has a body portion 54, an extender acceptor 55 to accept the extender from the facet base; a body which includes a clamp end 56, 57 and a conduit that transport a fixably adjustable rod 58 with a clamping means 59 on a far end of said rod, opposed from said body and said clamp.

The iterations and embodiments of the invention are presented in their general format, but it is recognized that those skilled in the art may evolve and demonstrate other embodiments which are obvious when viewed in the face of these disclosures; clearly, all similar embodiments and iterations are within the spirit and scope of the invention.

What is claimed is:

1. An apparatus for diagnosing pain in human spines comprising a vertebrae anchoring apparatus comprising: a facet anchor base and a transverse process claw, a shaft connects a leading end of said transverse process claw to a trailing end; the trailing end being coupled to said facet anchor base in such a fashion that said transverse process claw can be brought against a target bony facet surface, further comprising a spinous anchoring base where said spinous base includes a left cranial spinous quarter; a right cranial spinous quarter, a left caudal spinous quarter and a right caudal spinous quarter wherein said quarters are adjustably assemble-able together to form an ovoid ring which can be tightly secured against a spinous process, and where in no part of the apparatus intrudes into the vertebrae bone, wherein said facet anchor further comprises a facet coupling extension; and said spinous anchor further includes a spinous coupling extension and where said facet anchor further comprises a coupling peg with a shaft interconnecting said transverse process claw and said facet base and where said shaft includes means for fixing said shafts position, and where no part of the apparatus intrudes into the vertebrae bone.

2. The apparatus of claim 1 wherein said means for fixing is a series of corrugations.

3. The apparatus of claim 2 wherein said facet coupling extension is couple-able with a coupling modulator to said spinous coupling extension.

4. The apparatus of claim 3 for stabilizing vertebrae of the human spine comprising an extendor; and a bracket block; wherein said spinous anchor, said extendor and said bracket block are configured to stabilize the L5-S1 joint, where no part of the apparatus intrudes into the vertebrae bone.

5. An apparatus for diagnosing pain in human spines comprising a vertebrae anchoring apparatus comprising: a spinous anchoring base where said spinous base includes a left cranial spinous quarter; a right cranial spinous quarter, a left caudal spinous quarter and a right caudal spinous quarter wherein said quarters are adjustably assemble able together to form an ovoid ring which can be tightly secured against a spinous process, where no part of the apparatus intrudes into the vertebrae bone, the apparatus further comprising a spinous coupling extension and a second spinous anchoring base where said second spinous base includes a left cranial spinous quarter; a right cranial spinous quarter, a left caudal spinous quarter and a right caudal spinous quarter wherein said quarters are adjustably assemble able together to form an ovoid ring which can be tightly secured against a spinous process, and said second spinous anchoring base further comprises a coupling extension couple-able with a coupling modulator to said first spinous coupling extension, where no part of the apparatus intrudes into the vertebrae bone.

* * * * *